(12) United States Patent
Coiseur

(10) Patent No.: US 12,178,519 B2
(45) Date of Patent: Dec. 31, 2024

(54) DEPTH CONTROL INSTRUMENT GUIDE FOR ROBOTIC SURGERY

(71) Applicant: MedTech S.A., Montpellier (FR)

(72) Inventor: Florian Coiseur, Lattes (FR)

(73) Assignee: MedTech S.A., Montpellier (FR)

( * ) Notice: Subject to any disclaimer, the term of this patent is extended or adjusted under 35 U.S.C. 154(b) by 953 days.

(21) Appl. No.: 17/070,547

(22) Filed: Oct. 14, 2020

(65) Prior Publication Data

US 2021/0113275 A1 Apr. 22, 2021

Related U.S. Application Data

(60) Provisional application No. 62/923,107, filed on Oct. 18, 2019.

(51) Int. Cl.
*A61B 34/20* (2016.01)
*A61B 34/30* (2016.01)
(Continued)

(52) U.S. Cl.
CPC .............. *A61B 34/20* (2016.02); *A61B 34/30* (2016.02); *A61B 2017/00221* (2013.01);
(Continued)

(58) Field of Classification Search
CPC ...... A61B 2090/062; A61B 2090/0811; A61B 34/20; A61B 34/30; A61B 2034/2059; A61B 2090/035; A61B 2017/00221
See application file for complete search history.

(56) References Cited

U.S. PATENT DOCUMENTS 8,884,618 B2 11/2014 Mahfouz
9,675,461 B2 6/2017 Mahfouz
(Continued)

FOREIGN PATENT DOCUMENTS

CN 101308155 11/2008
CN 103895023 7/2014
(Continued)

OTHER PUBLICATIONS

"Canadian Application Serial No. 3,157,125, Examiners Rule 86(2) Report mailed May 26, 2023", 4 pgs.
(Continued)

*Primary Examiner* — Chao Sheng
(74) *Attorney, Agent, or Firm* — SCHWEGMAN LUNDBERG & WOESSNER, P.A.

(57) ABSTRACT

An instrument holder system comprises a guide body comprising first and second ends, and a passage extending between the first and second ends along an axis to receive an instrument, and a mechanical or electro-mechanical measuring device comprising an attachment body for coupling to the guide body, a probe to extend into a trajectory of the passage to contact the instrument and generate positional data, and, optionally, a control device coupled to the probe to receive the positional data. A method of determining a position of an instrument relative to an instrument holder comprises inserting the instrument into a passage of the instrument holder, moving the instrument into contact with a sensing element, moving a tip of the instrument out of the instrument holder to cause movement of the sensing element, and correlating movements of the sensing element to distances the tip extends out of the instrument holder.

24 Claims, 13 Drawing Sheets

(51) Int. Cl.
*A61B 17/00* (2006.01)
*A61B 90/00* (2016.01)

(52) U.S. Cl.
CPC . *A61B 2034/2059* (2016.02); *A61B 2090/035* (2016.02); *A61B 2090/062* (2016.02); *A61B 2090/0811* (2016.02)

(56) References Cited

U.S. PATENT DOCUMENTS

| | | |
|---|---|---|
| 2006/0041232 A1 | 2/2006 | Stearns et al. |
| 2009/0326463 A1 | 12/2009 | Ross |
| 2010/0240958 A1 | 9/2010 | Abrams et al. |
| 2012/0190982 A1* | 7/2012 | Hyoun ............... A61B 17/3403 600/439 |
| 2016/0302653 A1 | 10/2016 | Inoue |
| 2017/0071691 A1 | 3/2017 | Crawford et al. |
| 2017/0312035 A1 | 11/2017 | May et al. |
| 2018/0338797 A1 | 11/2018 | Moore et al. |
| 2018/0360479 A1 | 12/2018 | Hofmann et al. |

FOREIGN PATENT DOCUMENTS

| | | |
|---|---|---|
| CN | 105848552 A | 8/2016 |
| CN | 108472099 A | 8/2018 |
| CN | 109108982 | 1/2019 |
| CN | 114650784 A | 6/2022 |
| EP | 2478856 A1 | 7/2012 |
| JP | H07255727 A * | 10/1995 |
| WO | WO-9810387 A2 | 3/1998 |
| WO | WO-2015061638 A1 | 4/2015 |
| WO | WO-2021074450 A1 | 4/2021 |

OTHER PUBLICATIONS

"Canadian Application Serial No. 3,157,125, Response filed Sep. 14, 2023 to Examiners Rule 86(2) Report mailed May 26, 2023", 16 pgs.

"European Application Serial No. 20797414.8. Response to Communication pursuant to Rules 161(1) and 162 EPC filed Dec. 6, 2022", 31 pgs.

"International Application Serial No. PCT/EP2020/079397, International Search Report mailed Mar. 25, 2021", 7 pgs.

"International Application Serial No. PCT/EP2020/079397, Invitation to Pay Additional Fees mailed Feb. 1, 2021", 19 pgs.

"International Application Serial No. PCT/EP2020/079397, Written Opinion mailed Mar. 25, 2021", 15 pgs.

"Chinese Application Serial No. 202080072853.X, Office Action mailed Jun. 13, 2024", w/ English Translation, 22 pgs.

"Chinese Application Serial No. 202080072853.X, Office Action mailed Oct. 29, 2024", w English translation, 25 pgs.

* cited by examiner

DEPTH CONTROL INSTRUMENT GUIDE FOR ROBOTIC SURGERY

CLAIM OF PRIORITY

This application claims the benefit of U.S. Provisional Patent Application Ser. No. 62/923,107, filed on Oct. 18, 2019, the benefit of priority of which is claimed hereby, and which is incorporated by reference herein in its entirety.

TECHNICAL FIELD

This document pertains generally, but not by way of limitation, to devices and methods for robot-assisted surgical procedures, such those involving the use of articulating robotic arms that can be moved about multiple axes. More specifically, but not by way of limitation, the present application relates to holders and guides that can be used to position instruments relative to a robotic arm.

BACKGROUND

Imaging of anatomical features can be useful in preparing for and performing surgical procedures. In some surgical procedures it can be desirable to register the shape of the anatomy in the obtained images with another frame of reference, such as the physical space of an operating room. The physical space of the operating room can be correlated to a frame of reference for a robotic surgical system. Robotic surgical arms are used to hold various instruments in place in a desired orientation relative to both the anatomy and operating room during a procedure so that movement of an instrument in the operating room relative to the anatomy can be tracked on the anatomic imaging based on movement of the robotic surgical arm. It is, therefore, desirable to precisely mount instruments to the robotic surgical arm. Means for measuring a position of an instrument relative to an instrument holder are described in Pub. No. WO 2015/061638 A1 to Crawford et al.

OVERVIEW

The present inventors have recognized, among other things, that problems to be solved with traditional robotic instrument holders can include knowing the relative position of an instrument within an instrument holder relative to a robotic arm holding the instrument. During surgeries involving a robotic surgical system, it can be desirable to precisely guide a medical instrument along a planned trajectory based on medical images. In order to maintain the trajectory of the instrument, surgeons use guide tubes or other devices that are mounted to a robotic surgical arm. Once the instrument is aligned along the desired trajectory, the robotic arm becomes immobilized and the instrument is moved along the trajectory through the instrument holder. Since the robot arm is not moving and the instrument is not attached on it, the precise position of the instrument cannot be determined via the location of the robotic arm. Previous attempts to determine the position of the instrument include attaching a tracking device to the instrument that can be tracked in a coordinate system synched to the coordinate system of the robotic arm. However, optical navigation systems require line-of-sight with the instrument to be maintained in order to obtain accurate position information. Other attempts to determine position of an instrument relative to the instrument holder involve using sensors in the instrument holder that read information off the instrument, as are described in the aforementioned publication to Crawford et al. Such systems, however, require the use instruments that are compatible with the sensor. As such, the instrument typically must include appropriate visual indicia (e.g., coated markers such as contrast or color marks or gradients) for optical reading or include metallic indicia (e.g., embedded magnetic strips or coils) for magnetic reading. Thus, such systems are not compatible with a wide variety of conventional instruments or off-the-shelf instruments, which can increase the cost and complexity of the instruments.

The present subject matter can provide a solution to these and other problems, such as by providing an instrument holder having a measuring device that can determine position information of conventional instruments and non-conventional instruments (e.g., those including visual or magnetic indicia). More particularly, the present subject matter can provide an instrument holder that includes a mechanical or electro-mechanical device for determining position of the instrument independent of features of the instrument in order to accommodate off-the-shelf and conventional (e.g., non-marked) instrumentation.

The present subject matter relates to medical instrument holder devices, such as for robotic surgical systems, that have mechanical or electro-mechanical position readers or sensors that can physically contact or engage the instrument while the instrument is inserted in or proximate to the position holder. Thus, in examples, the medical instrument holder devices of the present disclosure facilitate reading position information from any type of instrument without requiring special instruments compatible with the mechanical or electro-mechanical position reader. The position readers allow for precise alignment of the instrument relative to the position holder, thereby allowing the depth that a tip of an instrument is extended beyond the instrument holder, e.g., into a patient to be known and correlated to a coordinate system of the robotic surgical system.

In an example, an instrument holder system can comprise a guide body and a mechanical or electro-mechanical measuring device. The guide body can comprise a first end, a second end, and a passage extending between the first and second ends along an axis to receive an instrument. The measuring device can comprise an attachment body for coupling to the guide body, a probe configured to extend into a trajectory of the passage to contact the instrument and generate positional data and, optionally, a control device coupled to the probe and configured to receive the positional data.

In another example, a method of determining a position of a surgical instrument relative to an instrument holder for a robotic surgical system can comprise inserting the surgical instrument into a passage of the instrument holder, moving the instrument into contact with a sensing element, moving a tip of the instrument out of the instrument holder to cause movement of the sensing element, and correlating movements of the sensing element to distances the tip extends out of the instrument holder.

This overview is intended to provide an overview of subject matter of the present patent application. It is not intended to provide an exclusive or exhaustive explanation of the invention. The detailed description is included to provide further information about the present patent application.

Figure 1:
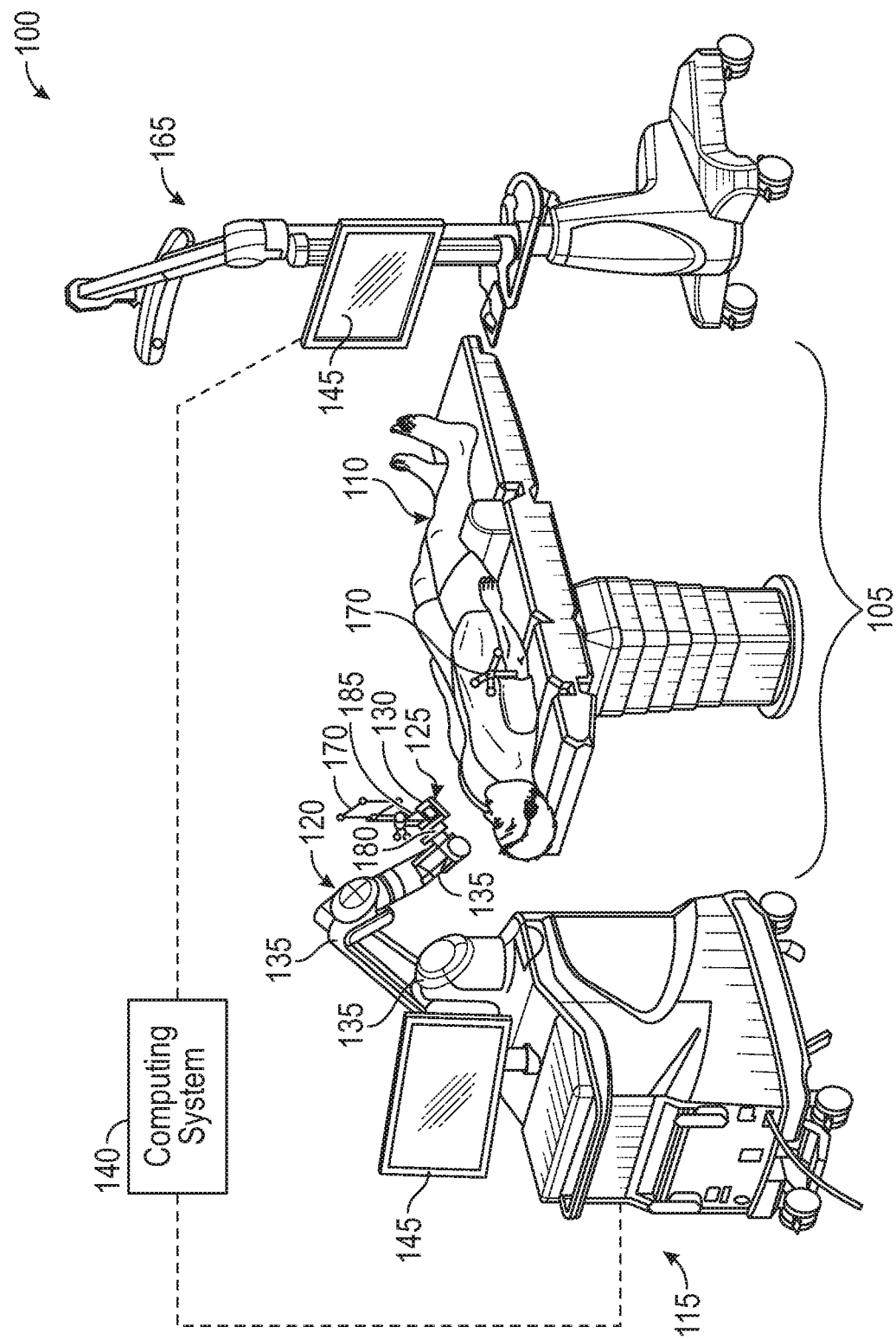
FIG. 1 is a diagrammatic view of an operating room including a robot-assisted surgical system comprising a robotic arm, a computing system and a tracking system.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

FIG. 1 illustrates surgical system 100 for operation on surgical area 105 of patient 110 in accordance with at least one example of the present disclosure. Surgical area 105 in one example can include a joint and, in another example, can be a bone. Surgical area 105 can include any surgical area of patient 110, including but not limited to the shoulder, head, elbow, thumb, spine, and the like. Surgical system 100 can also include robotic system 115 with one or more robotic arms, such as robotic arm 120. As illustrated, robotic system 115 can utilize only a single robotic arm. Robotic arm 120 can be a 6 degree-of-freedom (DOF) robot arm, such as the ROSA® robot from Medtech, a Zimmer Biomet Holdings, Inc. company. In some examples, robotic arm 120 is cooperatively controlled with surgeon input on the end effector or surgical instrument, such as surgical instrument 125. In other examples, robotic arm 120 can operate autonomously. While not illustrated in FIG. 1, one or more positionable surgical support arms can be incorporated into surgical system 100 to assist in positioning and stabilizing instruments or anatomy during various procedures.

Each robotic arm 120 can rotate axially and radially can receive a surgical instrument, or end effector, 125 at distal end 130. Surgical instrument 125 can be any surgical instrument adapted for use by the robotic system 115, including, for example, a guide tube, a holder device, a gripping device such as a pincer grip, a burring device, a reaming device, an impactor device such as a humeral head impactor, a pointer, a probe or the like. Surgical instrument 125 can be positionable by robotic arm 120, which can include multiple robotic joints, such as joints 135, that allow surgical instrument 125 to be positioned at any desired location adjacent or within a given surgical area 105. As discussed below, robotic arm 120 can be used with an instrument positioning device, e.g., instrument holder 200 (FIG. 2), to position an instrument in a known, desired or predetermined orientation relative to surgical area 105 based on a virtual coordinate system determined by computing system 140.

Robotic system 115 can also include computing system 140 that can operate robotic arm 120 and surgical instrument 125. Computing system 140 can include at least memory, a processing unit, and user input devices, as will be described herein. Computing system 140 and tracking system 165 can also include human interface devices 145 for providing images for a surgeon to be used during surgery. Computing system 140 is illustrated as a separate standalone system, but in some examples computing system 140 can be integrated into robotic system 115. Human interface devices 145 can provide images, including but not limited to three-dimensional images of bones, glenoid, joints, and the like. Human interface devices 145 can include associated input mechanisms, such as a touch screen, foot pedals, or other input devices compatible with a surgical environment.

Computing system 140 can receive pre-operative, intraoperative and post-operative medical images. These images can be received in any manner and the images can include, but are not limited to, computed tomography (CT) scans, magnetic resonance imaging (MRI), two-dimensional x-rays, three-dimensional x-rays, ultrasound, and the like. These images in one example can be sent via a server as files attached to an email. In another example the images can be stored on an external memory device such as a memory stick and coupled to a USB port of the robotic system to be uploaded into the processing unit. In yet other examples, the images can be accessed over a network by computing system 140 from a remote storage device or service.

After receiving one or more images, computing system 140 can generate one or more virtual models related to surgical area 105. Alternatively, computer system 140 can receive virtual models of the anatomy of the patient prepared remotely. Specifically, a virtual model of the anatomy of patient 110 can be created by defining anatomical points within the image(s) and/or by fitting a statistical anatomical model to the image data. The virtual model, along with virtual representations of implants, can be used for calculations related to the desired height, depth, inclination angle, or version angle of an implant, stem, surgical instrument, or the like related to be utilized in surgical area 105. In another procedure type, the virtual model can be utilized to determine insertion location, trajectory and depth for inserting an instrument. The virtual model can also be used to determine bone dimensions, implant dimensions, bone fragment dimensions, bone fragment arrangements, and the like. Any model generated, including three-dimensional models, can be displayed on human interface devices 145 for reference during a surgery or used by robotic system 115 to determine motions, actions, and operations of robotic arm 120 or surgical instrument 125. Known techniques for creating virtual bone models can be utilized, such as those discussed in U.S. Pat. No. 9,675,461, titled "Deformable articulating templates" or U.S. Pat. No. 8,884,618, titled "Method of generating a patient-specific bone shell" both by Mohamed Rashwan Mahfouz, as well as other techniques known in the art.

Computing system 140 can also communicate with tracking system 165 that can be operated by computing system 140 as a stand-alone unit. Surgical system 100 can utilize the Polaris optical tracking system from Northern Digital, Inc. of Waterloo, Ontario, Canada. Additionally, tracking system 165 can comprise the tracking system shown and described in Pub. No. US 2017/0312035, titled "Surgical System Having Assisted Navigation" to Brian M. May, which is hereby incorporated by this reference in its entirety. Tracking system 165 can monitor a plurality of tracking elements, such as tracking elements 170, affixed to objects of interest to track locations of multiple objects within the surgical field. Tracking system 165 functions to create a virtual three-dimensional coordinate system within the surgical field for tracking patient anatomy, surgical instruments, or portions of robotic system 115. Tracking elements 170 can be tracking frames including multiple IR reflective tracking spheres, or similar optically tracked marker devices. In one example, tracking elements 170 can be placed on or adjacent one or more bones of patient 110. In other examples, tracking elements 170 can be placed on robot robotic arm 120, surgical instrument 125, and/or an implant to accurately track positions within the virtual coordinate system associated with surgical system 100. In each instance tracking elements 170 can provide position data, such as patient position, bone position, joint position, robotic arm position, implant position, or the like.

Robotic system 115 can include various additional sensors and guide devices. For example, robotic system 115 can include one or more force sensors, such as force sensor 180. Force sensor 180 can provide additional force data or information to computing system 140 of robotic system 115. Force sensor 180 can be used by a surgeon to cooperatively move robotic arm 120. For example, force sensor 180 can be used to monitor impact or implantation forces during certain operations, such as insertion of an implant stem into a humeral canal. Monitoring forces can assist in preventing negative outcomes through force fitting components. In other examples, force sensor 180 can provide information on soft-tissue tension in the tissues surrounding a target joint. In certain examples, robotic system 115 can also include laser pointer 185 that can generate a laser beam or array that is used for alignment of implants during surgical procedures.

In order to ensure that computing system 140 is moving robotic arm 120 in a known and fixed relationship to surgical area 105 and patient 110, the space of surgical area 105 and patient 110 can be registered to computing system 140 via a registration process involving registering fiducial markers attached to patient 110 with corresponding images of the markers in patient 110 recorded preoperatively or just prior to a surgical procedure. For example, a plurality of fiducial markers can be attached to patient 110, images of patient 110 with the fiducial markers can be taken or obtained and stored within a memory device of computing system 140. Subsequently, patient 110 with the fiducial markers can be moved into, if not already there because of the imaging, surgical area 105 and robotic arm 120 can touch each of the fiducial markers. Engagement of each of the fiducial markers can be cross-referenced with, or registered to, the location of the same fiducial marker in the images. In additional examples, patient 110 and medical images of the patient can be registered in real space using contactless methods, such as by using a laser rangefinder held by robotic arm 120 and a surface matching algorithm that can match the surface of the patient from scanning of the laser rangefinder and the surface of the patient in the medical images. As such, the real-world, three-dimensional geometry of the anatomy attached to the fiducial markers can be correlated to the anatomy in the images and movements of instruments 125 attached to robotic arm 120 based on the images will correspondingly occur in surgical area 105.

Subsequently, other instruments and devices attached to surgical system 100 can be positioned by robotic arm 120 into a known and desired orientation relative to the anatomy. For example, robotic arm 120 can be coupled to an instrument holder including a depth control device of the present disclosure. Robotic arm 120 can move the instrument holder and depth control device into different positions relative to anatomy of the patient such that an axis of the adjustable instrument holder extends along a desired orientation relative to the anatomy. The depth control devices of the present application can enable surgical system 100 to know the location of an instrument relative to the instrument holder so that the precise position of the instrument relative to robotic arm 120 can be determined, without the use of an optical tracking system of manual efforts.

Figure 2:
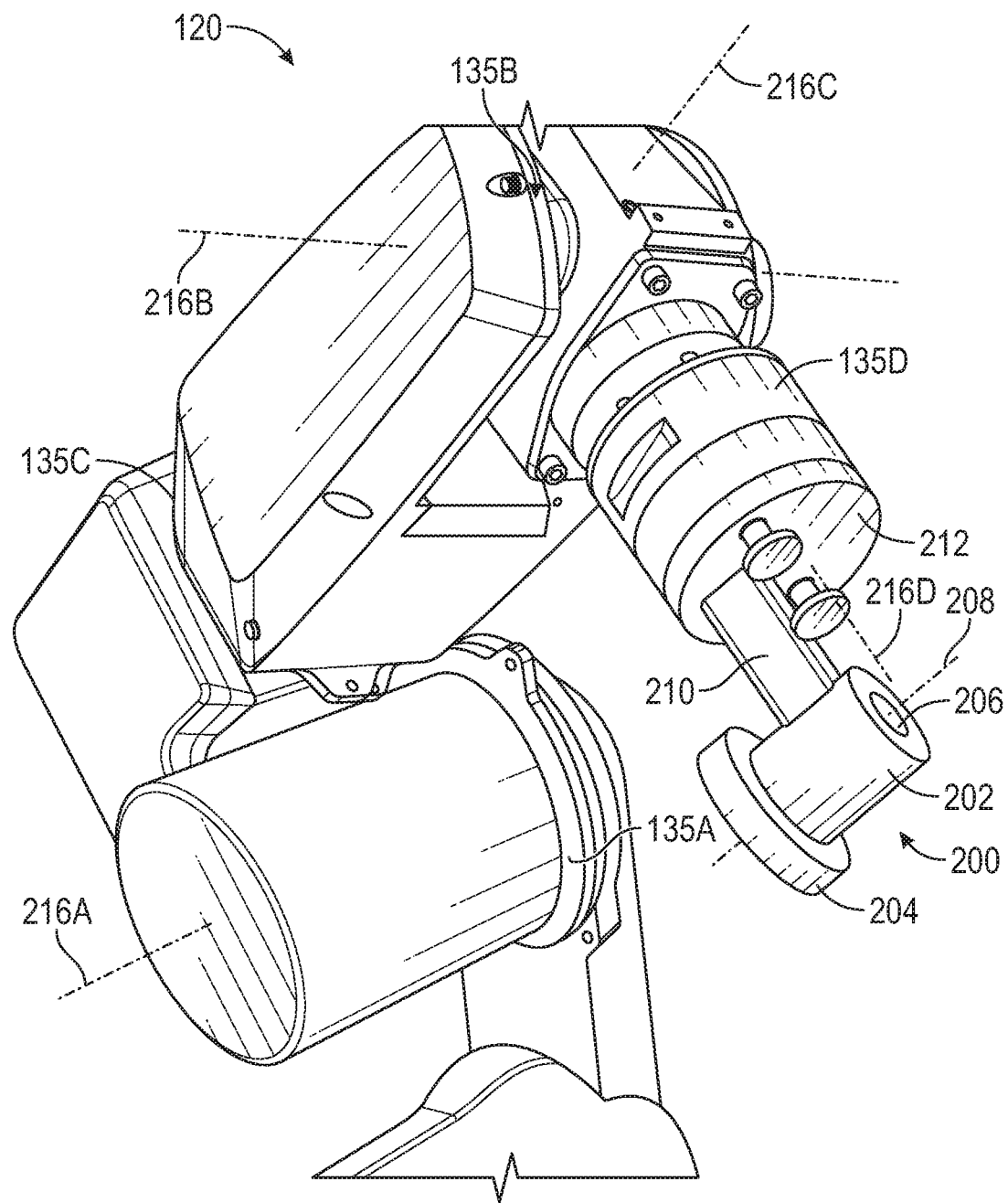
FIG. 2 is a schematic view of the robotic arm of FIG. 1 including an instrument holder configured to support or guide an instrument along an axis with a depth control device.

FIG. 2 is a schematic view of robotic arm 120 of FIG. 1 including instrument holder 200, can be positioned by robotic arm 120 relative to surgical area 105 (FIG. 1) in a known orientation. Instrument holder 200 can comprise guide body 202 and measuring device 204. Passage 206 can extend through guide body 202 and measuring device 204 along axis 208. Instrument holder 200 can be coupled to robotic arm 120 via extension 210 and mounting plate 212.

Robotic arm 120 can include joint 135A that permits rotation about axis 216A, joint 135B that can permit rotation about axis 216B, joint 135C that can permit rotation about axis 216C and joint 135D that can permit rotation about axis 216D.

In order to position instrument holder 200 relative to anatomy of patient 110 (FIG. 1), surgical system 100 (FIG. 1) can manipulate robotic arm 120 automatically by computing system 140 or a surgeon manually operating computing system 140 to move instrument holder 200 to the desired location, e.g., a location called for by a surgical plan to align an instrument relative to the anatomy. For example, robotic arm 120 can be manipulated along axes 216A-216D to position passage 208 of instrument holder 200 along a trajectory for which an instrument is to be guided.

Robotic arm 120 can be separately registered to the coordinate system of surgical system 100, such via use of a tracking element 170. Fiducial markers can additionally be separately registered to the coordinate system of surgical system 100 via engagement with a probe having a tracking element 170 attached thereto. As such, some or all of the components of surgical system 100 can be individually registered to the coordinate system and, if desired, movement of such components can be continuously or intermittently tracked with a tracking element 170.

It can be a difficult task to ensure instruments attached to robotic arm 120 are accurately aligned with and positioned relative to patient 110, particularly if the instrument needs to be individually manipulated during the procedure, such as by intervention of personnel including a surgeon. For example, sometimes robotic arm 120 is positioned to provide the proper alignment of an instrument, e.g., a guide pin, that needs to be inserted into the patient. Thus, robotic arm 120 can automatically provide a trajectory for an instrument, while the surgeon manually provides the motive force for the instrument. However, once the surgeon moves the instrument relative to robotic arm 120, the precise location of the instrument, e.g., the location of the tip of the instrument in the coordinate system, can become lost or obfuscated, and surgical system 100 will not be able to reproduce the location of said tip in imaging of the patient.

In some robotic procedures instruments can be separately tracked using an optical navigation system that, under ideal conditions, alleviate the need for precisely maintaining axis 208 and the location of an instrument along axis 208 through a surgical procedure or surgical task, as the optical navigation system can provide the surgical computer system information to compensate for any changes. However, as optical navigation systems require line-of-sight with the instruments to be maintained, there is a significant advantage in not requiring instruments to be navigated (or at least not constantly navigated). Accordingly, the ability to precisely maintain axis 208 and position along axis 208 provides the additional advantage of at least reducing, and possibly eliminating, the need to navigate instruments during a robotic procedure.

In order to improve the ability to determine the location of instruments within the coordinate system, such as along axis 208, the present application describes various measuring devices (e.g., depth control devices, sensing devices, mechanical position determining devices, electro-mechanical positioning devices) that can determine the position of an instrument relative to an instrument holder without requiring line-of-sight or specialty instruments, such that the position of the instrument relative to robotic arm 120 and the coordinate system can be determined.

Figure 3:
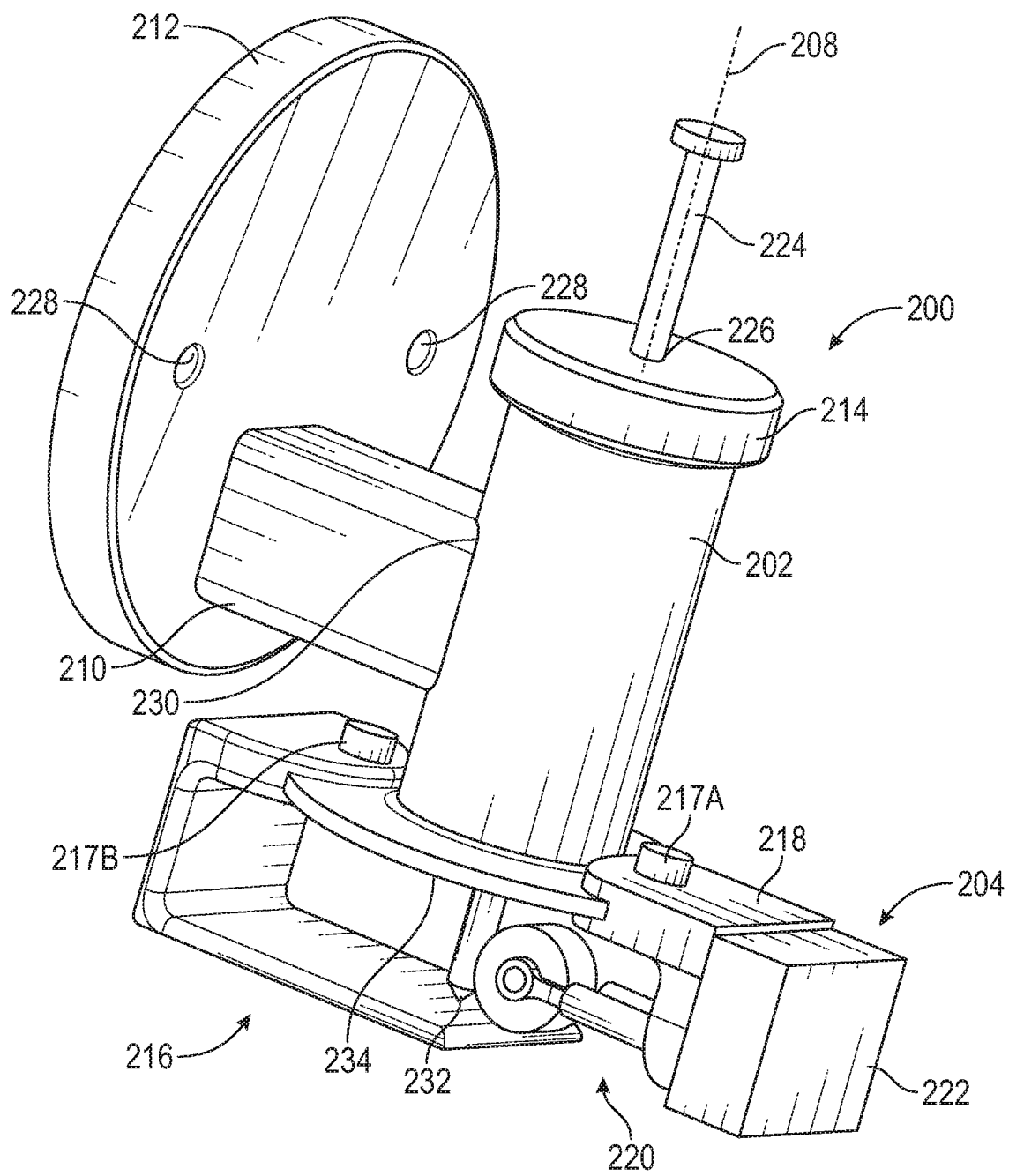
FIG. 3 is a perspective view of an instrument holder having a depth control device for aligning and holding in-place various medical instruments during surgeries performed with a surgical robot, such as the robot-assisted surgical system of FIGS. 1 and 2.

FIG. 3 is a perspective view of instrument holder 200 comprising guide body 202 and measuring device 204. Passage 206 (FIG. 2) can extend through guide body 202 and measuring device 204 along axis 208. Instrument holder 200 can be coupled to robotic arm 120 via extension 210 and mounting plate 212. Instrument holder 200 can further comprise instrument adapter 214 and calibration module 216. Measuring device 204 and calibration module 216 can be affixed to guide body 202 via fasteners 217A and 217B, respectively. Measuring device 204 can comprise attachment body 218, probe 220 and control device 222. Instrument holder 200 can be used in conjunction with instrument 224. Instrument holder 200 and instrument adapter 214 can comprise devices for holding an instrument, such as medical instruments including catheters, cannulas and guidewires.

Instrument adapter 214 can be configured to be inserted into passage 206 (FIG. 2) of guide body 202. Instrument adapter 214 can include passage 226 for receiving instrument 224. Passage 226 in instrument adapter 214 can be positioned to align with axis 208 (FIG. 2) such that passage 226 and passage 206 are concentric. Robotic arm 120 can be configured to position guide body 202 and hence instrument adapter 214 in a fixed orientation such that axis 208 is aligned relative to a patient in a desired orientation, such as an orientation pre-operatively or intra-operatively planned according to a surgical plan.

Mounting plate 212 can be mounted to robotic arm 120 (FIG. 2) such as by inserting threaded fasteners into bores 228. Extension 210 can be coupled to mounting plate 212 to provide a mounting arm for coupling with instrument holder 200. Extension 210 can include seat 230 having a semi-circular or circular arc length shape to receive and mate with guide body 202. Extension 210 and guide body 202 can be coupled using any suitable means, such as fasteners (e.g., fastener 304 of FIG. 8) or metallurgical bonding. Extension 210 can extend along an axis that is perpendicular to axis 208. Extension 210 can be configured to align passage 206 extending through guide body 202 at a known position relative to bores 228 such that the position of passage 206 to robotic arm 120 is in a known, e.g., known to computing system 140, orientation. Thus, as robotic arm 120 moves instrument holder 200, the position of instrument holder 200 relative to surgical area 105 (FIG. 1) will also be known.

After instrument holder 200 is attached to robotic arm (FIG. 2) via mounting plate 212, instrument adapter 214, calibration module 216 and measuring device 204 can be attached to guide body 202. Instrument adapter 214, calibration module 216 and measuring device 204 can be assembled to main body 202 in any order. Instrument adapter 214, calibration module 216 and measuring device 204 can be used to determine the relative position of instrument 224 to instrument holder 200, such as how far a tip 232 of instrument 224 extends beyond an inferior end, e.g., bottom surface 234, of main body 202.

Figure 4:
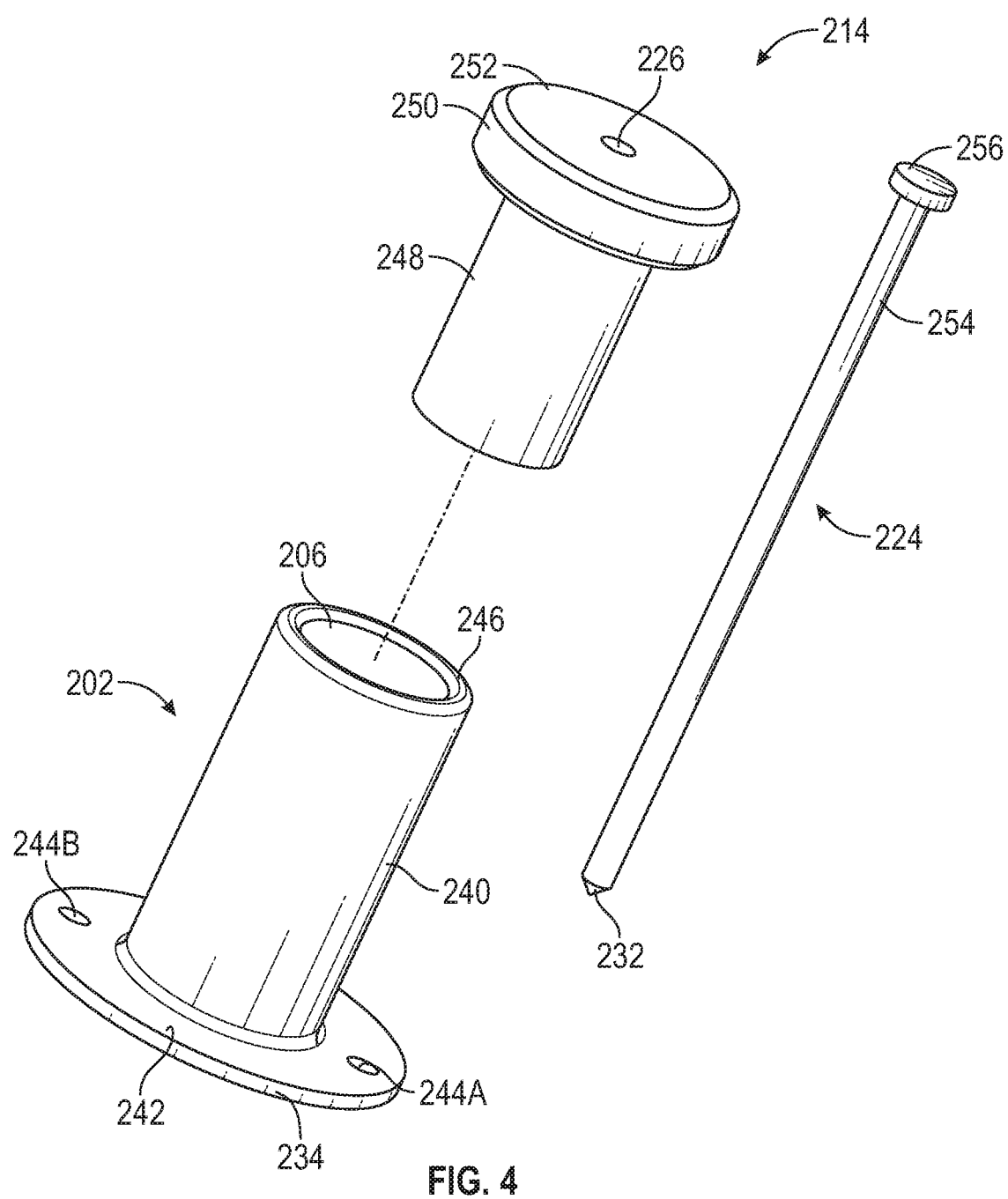
FIG. 4 is a perspective exploded view of a guide body, instrument adapter and an instrument of the instrument holder of FIG. 3.

FIG. 4 is a perspective exploded view of guide body 202, instrument adapter 214 and instrument 224 of instrument holder 200 of FIG. 3. Guide body 202 can comprise guide tube 240, mounting flange 242, bores 244A and 244B, top surface 246 and bottom surface 234. Guide tube 240 can define passage 206. Instrument adapter 214 can comprise adapter tube 248, stop flange 250, top surface 252 and passage 226. Instrument 224 can comprise shaft 254, flange 256 and tip 232.

Figure 8:
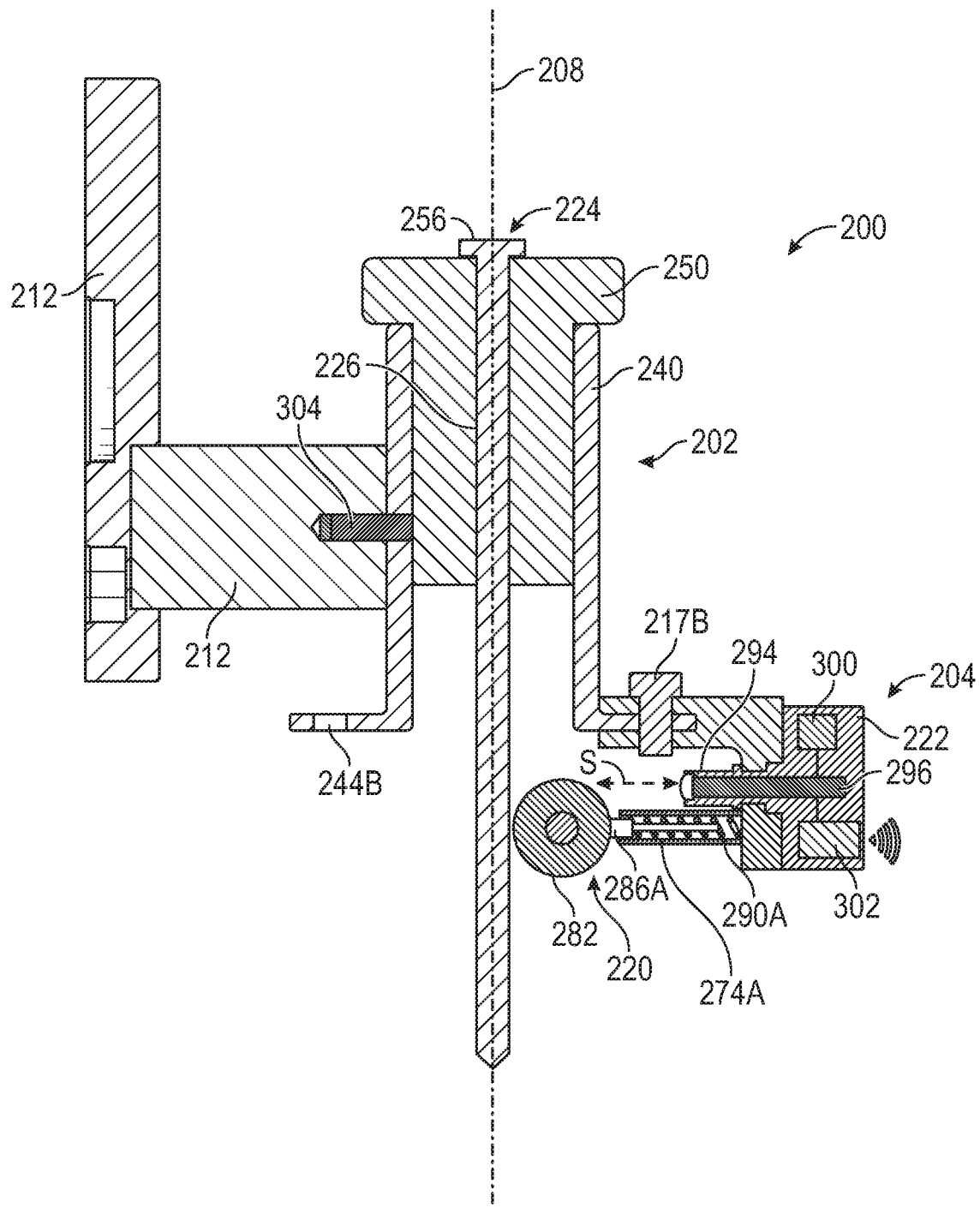
FIG. 8 is a side cross-sectional view of the instrument holder of FIG. 7 with the calibration module removed.

Adapter tube 248 can have an outer diameter sized to closely mate with the inner diameter of passage 206. Passage 226 can be centered within adapter tube 248. As such, passage 226 can be positioned concentric with passage 206 via placement of adapter tube 248 within guide tube 240. Stop flange 250 can have a diameter larger than that of passage 206, and guide tube 240, to prevent adapter tube 248 from passing completely through guide tube 240. As such, stop flange 250 can rest on a superior end, e.g., top surface 246, of guide tube 240. In examples, adapter tube 248 can be friction-fit into guide tube 240. Adapter tube 248 can be approximately equal in length to guide tube 240. However, as shown in FIG. 8, adapter tube 248 can be shorter than guide tube 240 to, for example, not interfere with tip 232 extending below bottom surface 234.

Shaft 254 can have an outer diameter sized to closely mate with the inner diameter of passage 226. As such, shaft 254 can be centered within passage 226 and instrument 224 can be centered within instrument holder 200. Shaft 254 can be longer than the length of guide tube 240 to allow tip 232 to extend out of, e.g., beyond bottom surface 234, guide tube 240. Stop flange 256 can have a diameter larger than that of shaft 254 and passage 226 to prevent instrument 224 from passing completely through instrument adapter 214. As such, stop flange 256 can rest on a superior end, e.g., top surface 252, of instrument adapter 214. In examples, shaft 254 can be friction-fit into passage 226 such that instrument 224 can remain in place within instrument adapter without shaft 254 freely sliding into passage 226. As such, instrument 224 can be held in-place within instrument adapter 214 in a desired position. For example, tip 232 can be held by frictional engagement between shaft 254 and adapter tube 248 inside passage 226 until a surgeon is ready to advance tip 232 toward a patient, such as by manually pushing on flange 256.

Mounting flange 242 can extend from bottom surface 234 of guide tube 240 and, as such, can have an outer diameter larger than guide tube 240. Flange 242 can provide a platform for mounting other components to guide body 202. Flange 242 can extend completely around the perimeter of guide tube 240 to allow attachment at any location around the circumference of guide tube 240. However, mounting flange 242 can include bores 244A and 244B to facilitate attachment of additional components at specific locations. In examples, bores 244A and 244B are located at opposing locations on mounting flange 242, e.g. one-hundred-eighty degrees apart, to receive calibration module 216 and measuring device 204.

Figure 5:
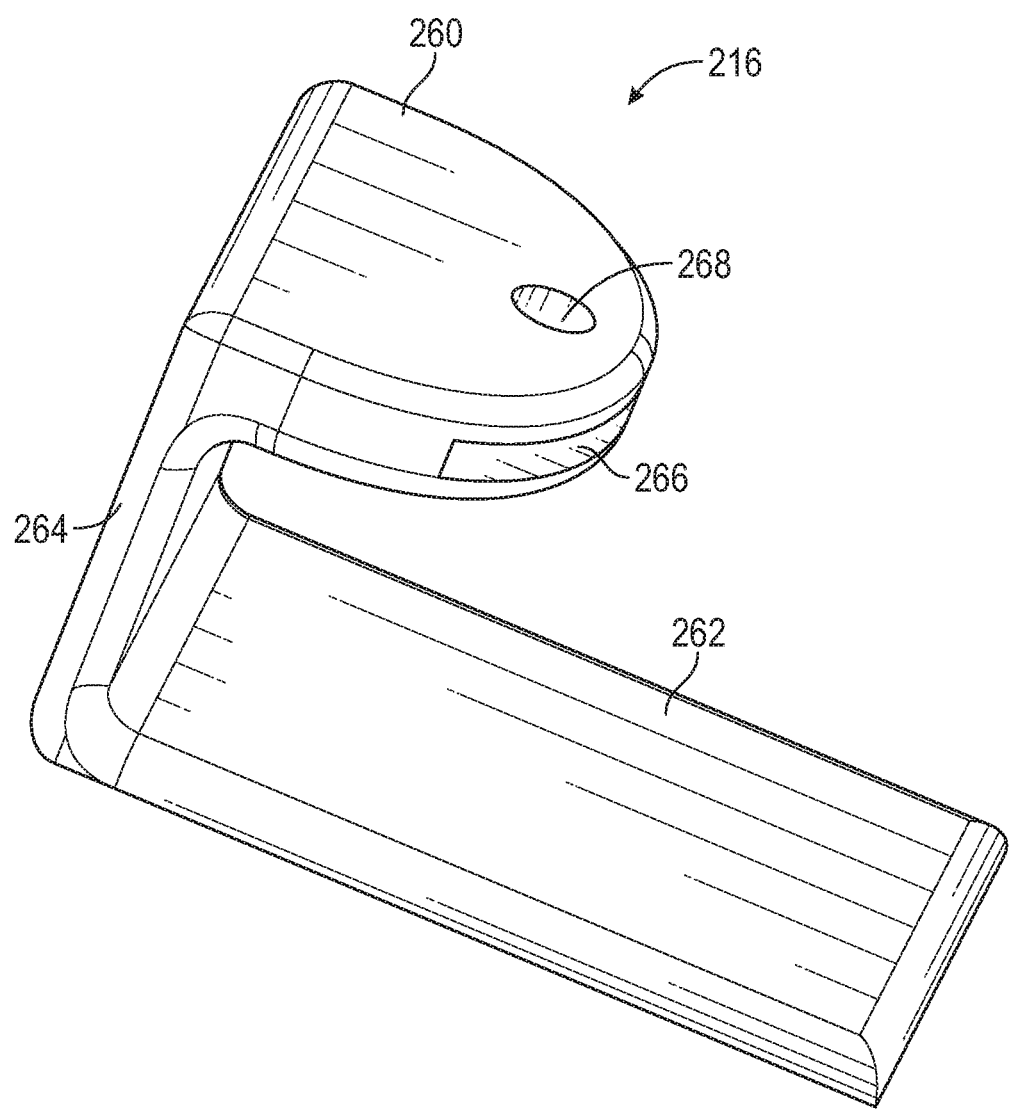
FIG. 5 is a perspective view of a calibration module of the instrument holder of FIG. 3.

FIG. 5 is a perspective view of calibration module 216 of instrument holder 200 of FIG. 3. Calibration module 216 can comprise coupling portion 260, plate 262 and extension 264. Coupling portion 260 can comprise slot 266 and bore 268. Bore 268 can comprise upper and lower portions extending through opposite sides of slot 266. Coupling portion 260 can comprise a flange configured to mate with mounting flange 242 (FIG. 4) of guide body 202. Slot 266 can have a height sufficient to receive mounting flange 242 and that is sufficiently deep to allow one of bores 244A and 244B to align with bore 268. As such, one of fasteners 217A and 217B (FIG. 3) can be extended through one of bores 244A and 244B and bore 268 to secure calibration module 216 to guide body 202. Slot 266 and plate 262 can extend in parallel planes. Plate 262 can have a length sufficient to extend from extension 264 to axis 208 (FIGS. 2 and 3) such that plate 262 can oppose passage 226. Thus, plate 262 can be configured to engage any diameter of instrument that extends from passage 206, for different sizes of passage 226 of instrument adapter 214. Extension 264 can extend away from coupling portion 260 to space plate 262 a distance away from slot 266. The distance that plate 262 is positioned away from slot 266 can be a fixed distance that is predetermined and known, e.g., known to computing system 140 (e.g., stored in memory of computing system 140). As will be discussed below, plate 262 can be used to zero the position of instrument 224 relative to guide body 202.

Figure 6:
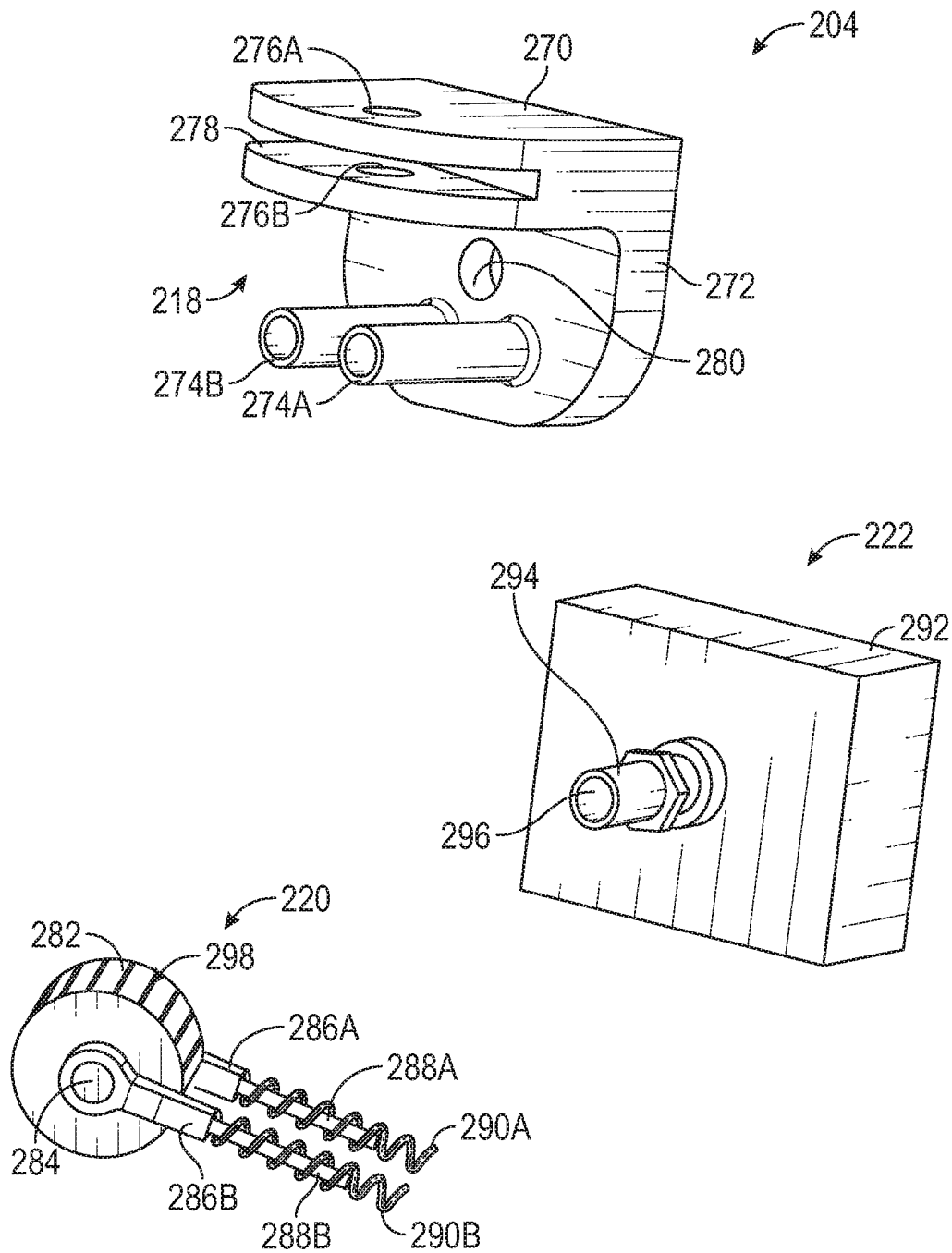
FIG. 6 is a perspective exploded view of a measuring device of the instrument holder of FIG. 3.

FIG. 6 is a perspective exploded view of measuring device 204 of instrument holder 200 FIG. 3. Measuring device 204 can comprise a sensing device or depth control device configured to determine or sense the position of instrument 224 relative to guide body 202, which can be used to control the distance that instrument 224 is extended from guide body 202, e.g. the depth that instrument is inserted into a patient. Measuring device 204 can comprise attachment body 218, probe 220 and control device 222. Attachment body 218 can comprise coupling portion 270, sensor bracket 272, and mounting posts 274A and 274B. Coupling portion 270 can comprise bores 276A and 276B and slot 278. Sensor bracket 272 can comprise bore 280. Probe 220 can comprise wheel 282, axle 284, mounting brackets 286A and 286B, posts 288A and 288B, and springs 290A and 290B. Control device 222 can comprise housing 292, tube 294 and sensor 296. Wheel 282 can include hash marks 298.

Coupling portion 270 can comprise a flange configured to mate with mounting flange 242 (FIG. 4) of guide body 202. Slot 278 can have a height sufficient to receive mounting flange 242 and that is sufficiently deep to allow one of bores 244A and 244B to align with bores 276A and 276B. As such, one of fasteners 217A and 217B (FIG. 3) can be extended through one of bores 244A and 244B and bores 276A and 276B to secure measuring device 204 to guide body 202.

Sensor bracket 272 can extend from coupling portion 270 to position bore 280 and mounting posts 274A and 274B in a position to face instrument 224 when extended out of passage 226 beyond bottom surface 234 (FIG. 3), e.g., to oppose extension 264 when both measuring device 204 and calibration module 216 are attached to mounting flange 242. Bore 280 can be configured to receive tube 294 of control device 222. As such, control device 222 can be mounted to an exterior surface of sensor bracket 272 such that tube 294 extends past an interior surface of sensor bracket 272 toward axis 208 (FIG. 3). Tube 294 can be threaded into bore 280 or can be held in place by fasteners, e.g., nuts, threaded onto tube 294. Sensor 296 can be located in tube 294 or housing 292 and can be configured to sense or emit signal S (FIG. 7) out of tube 294 toward axis 208. Housing 292 can comprise an enclosure or container to provide support and protection for components of control device 222. In addition to sensor 296, power module 300 and transmitter 302 (FIG. 8) can be stored in housing 292 and electrically coupled to sensor 296.

Probe 220 can comprise any suitable device for mechanically engaging instrument 224 and providing feedback to control device 222. In examples, probe 220 can be configured to make physical contact with instrument 224. In the illustrated example, probe 220 can comprise wheel 282 rotatable about or on axle 284. Thus, wheel 282 can be configured to rotate about an axis perpendicular to axis 208. Mounting brackets 286A and 286B can be configured to support wheel 282 via engagement with axle 284. Mounting brackets 286A and 286B can be coupled to posts 288A and 288B, respectively. Springs 290A and 290B can be configured to be positioned over posts 288A and 288B, respectively. Springs 290A and 290B and posts 288A and 288B can be configured to be inserted into mounting posts 274A and 274B, respectively. As such, mounting posts 274A and 274B can be configured as tubes having inner diameters larger than springs 290A and 290B. Posts 288A and 288B can be configured to slide within mounting posts 274A and 274B, respectively, to form a sliding bracket that can allow wheel 282 to be displaceable relative to axis 208. Springs 290A and 290B, or any other suitable biasing element, can be configured to bias wheel 282 toward axis 208. Springs 290A and 290B, posts 288A and 288B and mounting posts 274A and 274B can be configured to allow wheel 282 to traverse anywhere between contact of wheel 282 with axis 208 to a distance away from axis 208 to accommodate the largest sized instrument positionable within guide tube 240. In other words, wheel 282 can have a stroke length equal to, or greater than, the radius of guide tube 240. Springs 290A and 290B, posts 288A and 288B and mounting posts 274A and 274B can be assembled and secured by any means suitable to allow functionality described herein.

Figure 7:
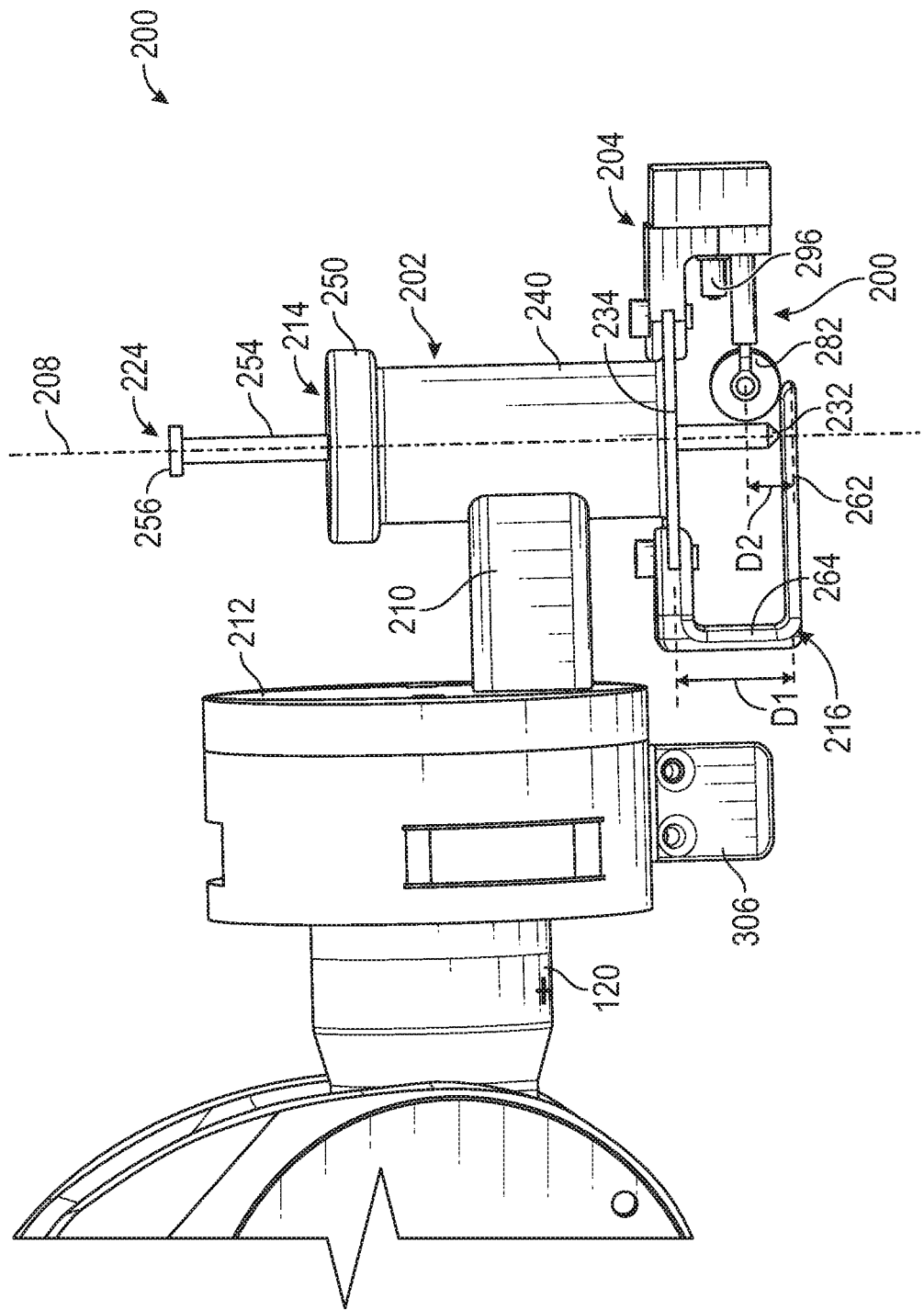
FIG. 7 is a side view of the instrument holder of FIG. 3 attached to the robotic arm of FIGS. 1 and 2 and showing the instrument inserted through the guide body to engage the calibration module.

FIG. 7 is a side view of instrument holder 200 of FIG. 3 attached to robotic arm 120 of FIGS. 1 and 2 and showing instrument 224 inserted through guide body 202 to engage calibration module 216. Plate 262 of calibration module 216 can be positioned opposite guide body 240 such that plate 262 can be engaged by instrument 224. Extension 264 can position plate 262 first distance D1 from bottom surface 234. Wheel 282 can be configured to contact instrument 224 distance D2 below bottom surface 234. Distances D1 and D2 can be stored in memory of computing system 140 (e.g., memory 622 of FIG. 14 or memories 1704 and 1707 of FIG. 15). In the position of instrument 224 of FIG. 7, e.g., with tip 232 contacting plate 262, measuring device 204 can be calibrated or zeroed to set the distance of tip 232 from bottom surface 234. Calibration can comprise a user-interface function where a user of surgical system 100 engages control device 222 or human interface devices 145 (FIG. 1) to record the location of tip 232 at the time of calibration. The location of bottom surface 234 can be known by computing system 140 in the coordinate system of surgical system 100 due to, for example, surgical system 100 knowing the location of robotic arm 120. With measuring device 204 zeroed, computing system 140 can be set to know the location of tip 232 in the same coordinate system. Probe 220 can engage, e.g., contact, shaft 254 of instrument 224 to keep track of, e.g., determine and transmit to computing system 140, the position of tip 232 in the coordinate system as instrument 224 is moved along axis 208 in instrument holder 200.

FIG. 8 is a side cross-sectional view of instrument holder 200 of FIG. 7 with calibration module 216 removed. Instrument 224 is moved further into passage 226 relative to the position of instrument 224 of FIG. 8. Control device 222 can comprise housing 292, tube 294, sensor 296, power module 300 and communication device 302. Power module 300 can comprise any suitable device for providing electric power to control device 222. In examples, power module 300 can comprise a battery or an AC-to-DC converter for receiving power from an electrical outlet. Communication device 302 can comprise any suitable device for receiving information from sensor 296 and conveying the information to outside of control device 222. In examples, communication device 302 can include circuitry to perform wireless communications, such as low-energy Bluetooth, near-field communication (NFC), or IEEE 802.11 (Wi-Fi). In other examples, communication device 302 can communicate via wired connection to robotic arm at communication port 306 (FIG. 7), such as a cable connector that can be additionally used for other devices, such as force sensor 180. Sensor 296 can be configured to emit signal S to contact wheel 282. Signal S can be configured as a reader device to read hash marks 298 on wheel 282. Hash marks 298 can comprise colored markings, e.g., darkened lines, or physical structures, e.g., depressions or protrusions. The circumferential distance between hash marks 298 can be stored in memory of computing system 140, for example, so that surgical system 100 can correlate rotational movement of wheel 282 with linear translation of instrument 224 along axis 208. In examples, sensor 296 can comprise a laser emitter. Sensor 296 can be configured to count hash marks 298 as hash marks 298 pass through signal S as wheel 282 rotates.

Figure 9:
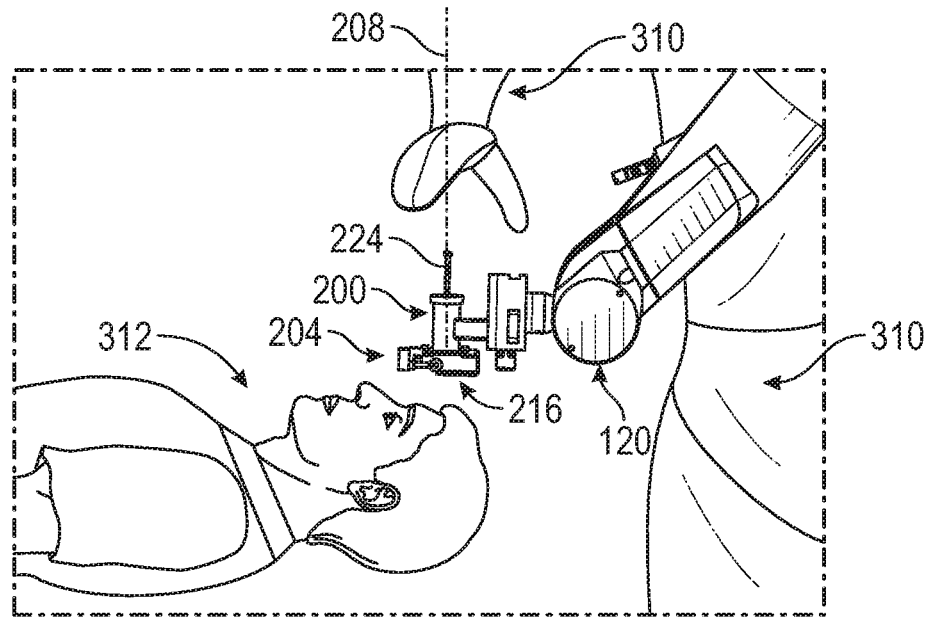
FIG. 9 is a schematic illustration showing the depth control device of the instrument holder of FIG. 3 being calibrated in an operating room environment.

FIG. 9 is a schematic illustration showing measuring device 204 of instrument holder 200 of FIG. 3 being calibrated in an operating room environment relative to surgeon 310 and patient 312. FIG. 9 illustrates the configuration of instrument holder 200 of FIG. 7 and shows that calibration module 216 and measuring device 204 can remain attached to instrument holder 200 to perform the calibration procedure. Robotic arm 120 can be positioned relative to patient 312 to align axis 208 with patient 312 is a desired orientation. Surgeon 310 can manually push instrument 224 down to engage plate 262 of calibration module 216 to perform the calibration or zeroing procedure. In other examples, calibration module 216 can be attached to robotic arm 120 and calibrated before robotic arm 120 positions instrument holder 200 in place.

Figure 10:
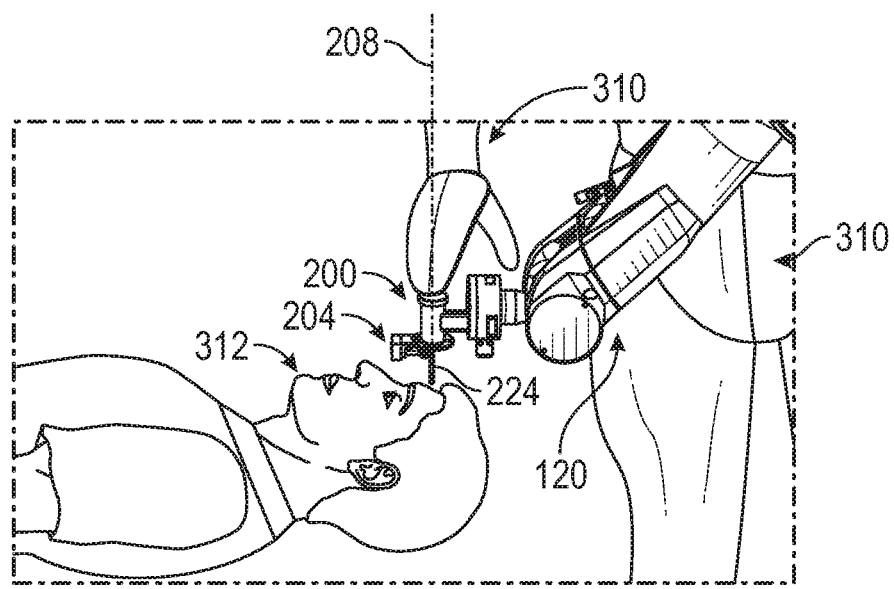
FIG. 10 is a schematic illustration showing the depth control device of the instrument holder of FIG. 3 being used to guide an instrument into engagement with a patient in the operating room environment.

FIG. 10 is a schematic illustration showing measuring device 204 of instrument holder 200 of FIG. 9 being used to guide an instrument 224 into engagement with patient 312 in the operating room environment. FIG. 10 illustrates the configuration of instrument holder 200 of FIG. 8 and shows that calibration module 216 can be removed to allow measuring device 204 to be used to perform a medical procedure. After the calibration procedure has been performed, calibration module 216 can be removed from instrument holder 200. Robotic arm 120 can hold instrument holder 200 in place along the desired trajectory of axis 208. Thus, surgeon 310 can manually push instrument into contact with or into patient 312. Measuring device 204 can be used by surgeon 310 to determine, via surgical system 100, the location of tip 232. Surgeon 310 can then advance instrument 224 according to a surgical plan to a desired depth. For example, surgeon 310 can consult human interface devices 145 to read a distance that tip 232 has been extended, or to view directly, in real time, the insertion of the instrument into a 3D model based on medical images. As discussed below, advancement of instrument 224 can additionally be automated, such as by surgeon 310 entering into human interface devices 145 a distance for tip 232 to be moved and a motorized version of measuring device 204, such as described below, can be used to move instrument 224.

Figure 11:
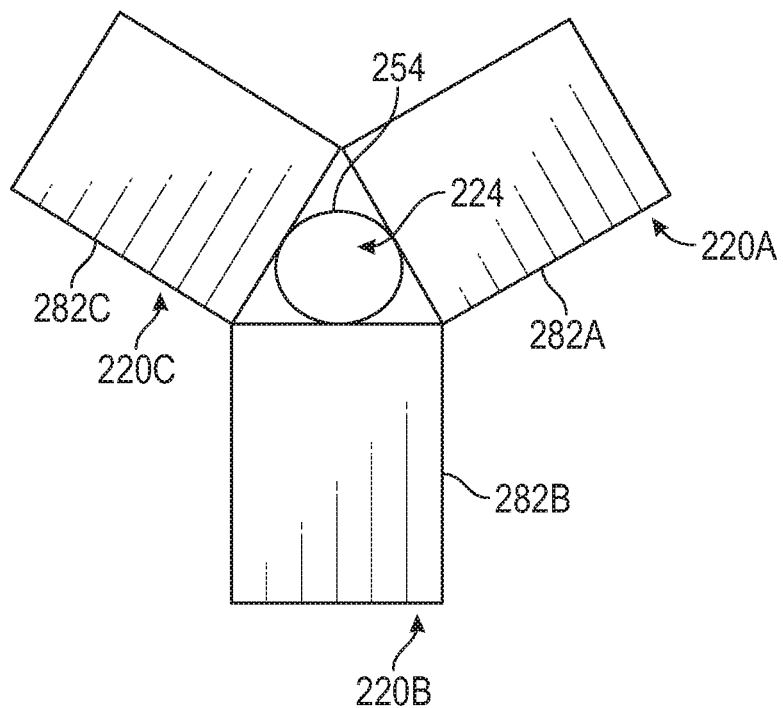
FIG. 11 is a schematic illustration showing an additional embodiment of the instrument holder described herein including multiple measuring devices.

FIG. 11 is a schematic illustration showing an additional embodiment of the instrument holders described herein including multiple probes 220A, 220B and 220C, including wheels 282A, 282B and 282C, respectively. Probes 220A, 220B and 220C can further include sensors, such as sensor 296, though not illustrated for simplicity. Multiple probes can be included in instrument holder 200 to provide redundancy. Furthermore, multiple probes can facilitate centering of instrument 224 on axis 208, such as by eliminating potential for a single probe to push instrument 224 off alignment with axis 208. FIG. 11 illustrates multiple probes of the same type, i.e., each including a wheel for direct mechanical engagement of instrument 224. However, any of the probes or measuring devices described herein can be combined in various combination to provide redundancy and stabilization to instrument 224.

Figure 12:
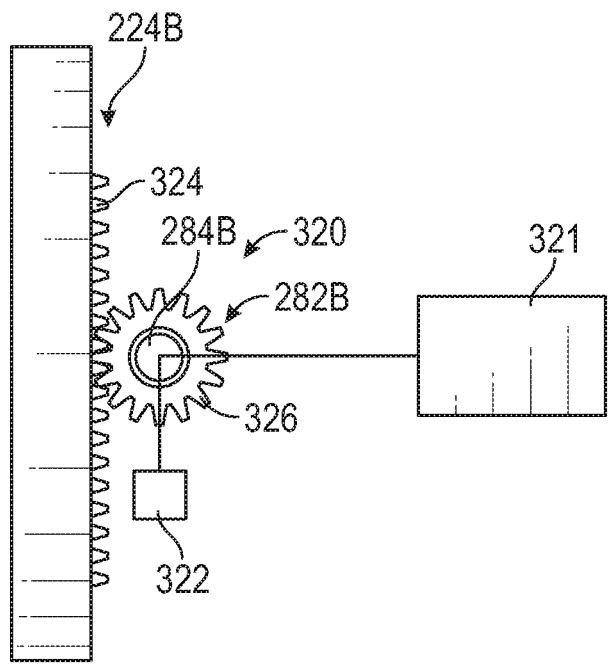
FIG. 12 is a schematic illustration of a position measuring device for use with compatible instruments via engagement of a rack and pinion engagement system.

FIG. 12 is a schematic illustration of mechanical position measuring device 320 for use with compatible instruments via engagement of a rack and pinion engagement system. Measuring device 320 can comprise motor 321 and encoder 322, as well as wheel 282B and axle 284B. The rack and pinion engagement system can include rack gear teeth 324 located on instrument 224B and pinion gear teeth 326 located on wheel 282B. Wheel 282B and axle 284B can be configured to operate within a probe similar to operation of wheel 282 and axle 284 in probe 220. As such, wheel 282B can be configured to rotate about an axis perpendicular to axis 208. Instrument 224B can be pushed down into passage 226 to mechanically engage wheel 282B. Passage 226 can include a cut-out or channel to accommodate teeth 324. Teeth 324 can engage teeth 326 of wheel 282B to become enmeshed. As such, rather than a frictional engagement, direct pushing of wheel 282B can occur via pushing of teeth 324 against teeth 326. Encoder 322 can be included in wheel 282B or axle 284B to record the rotational movement of wheel 282B. Such rotational movement can be correlated to the linear translation of instrument 224B to determine the position of the tip of instrument 224B, as is described herein. Encoder 232 can comprise an electro-mechanical rotary encoder device where the angular position or motion of axle 284 is converted to analog or digital output signals. An encoder, such as encoder 232, can additionally be provided within wheel 282 of FIGS. 3 and 6-8 to provide redundancy with sensor 296 or as an alternative to sensor 296.

In additional examples, wheel 282B can be driven by motor 320. Motor 320 can be used to move instrument 224B automatically without intervention from surgeon 310. For example, a button or switch on control device 222 or human interface devices 145 can be actuated by surgeon 310 to activate movement of motor 320 and cause linear movement of instrument 224B. Motor 320 can additionally be included in the other examples of instrument holders and measuring devices described herein.

Figure 13:
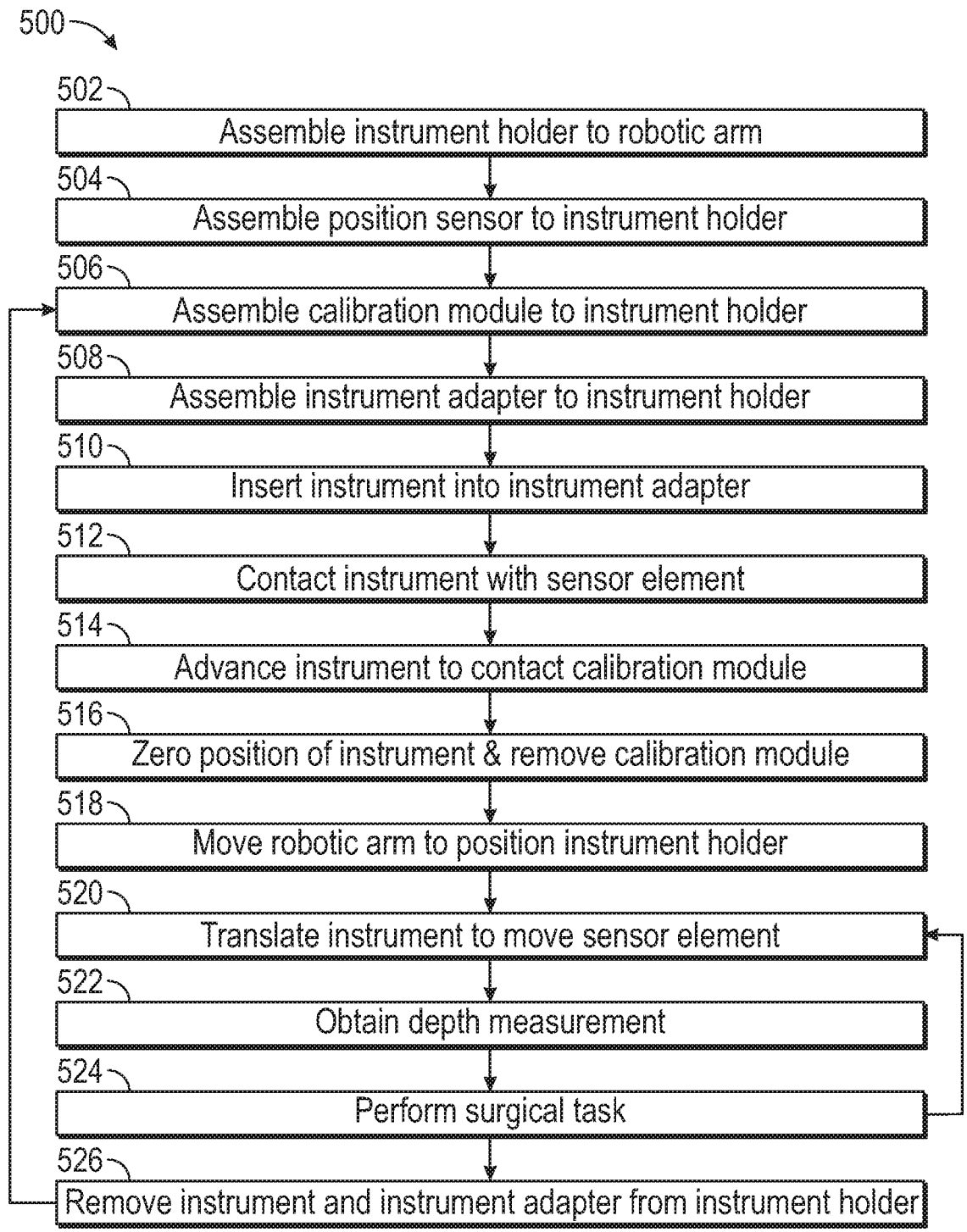
FIG. 13 is a flow chart illustrating steps of methods for assembling an instrument holder with a measuring device and a robotic surgical system, calibrating the measuring device of the instrument holder and using the instrument holder with the measuring device.

FIG. 13 is a flowchart illustrating actions or steps of methods or technique 500 for assembling instrument holder 200 with measuring device 204 and robotic surgical system 100, calibrating measuring device 204 with calibration module 216 and using instrument holder 200 with measuring device 204.

At step 502, instrument holder 200 can be assembled with robotic arm 120. For example, guide body 202 can be attached to extension 210 using fastener 304.

At step 504, a position sensor can be attached to instrument holder 200. For example, measuring device 204 can be attached to guide body 202 by positioning mounting flange 242 in slot 278 on attachment body 218. Measuring device 204 can be secured by inserting fastener 217A into bore 276A, through bore 244A and into bore 217B.

At step 506, calibration module 216 can be attached to instrument holder 200. For example, calibration module 216 can be attached to guide body 202 by positioning mounting flange 242 in slot 266 on coupling portion 260. Calibration module 216 can be secured by inserting fastener 217B into bore 268 and bore 244B.

At step 508, instrument adapter 214 can be attached to instrument holder 200. For example, adapter tube 248 can be inserted into passage 206 within guide tube 240. Instrument adapter 214 can be positioned so that stop flange 250 contacts top surface 246.

At step 510, instrument 224 can be inserted into passage 226 of instrument adapter 214. Instrument 224 can be positioned so that tip 232 remains within passage 226 above probe 220 for calibration and later deployment toward patient 312.

At step 512, instrument 224 can be advanced within passage 226 until instrument contacts wheel 282 of probe 220. For example, instrument 224 can be advanced within passage 226 so that tip 232 engages and then moves past wheel 282 of probe 220. Shaft 254 of instrument 224 can remain in contact with wheel 282. In particular, movement of shaft 254 against wheel 282 can cause rotation of wheel 282 about axle 284 via frictional engagement.

Thus, steps 502-512 can describe a method of assembling instrument holder 200 to robotic arm 120, including a sub-method of assembling measuring device 204, calibration module 216 and instrument adapter 214 to instrument holder 200.

At step 514, instrument 224 can be advanced within passage 226 so that tip 232 contacts calibration module 216. For example, shaft 254 can be advanced until tip 232 contacts plate 262.

At step 516, the position of instrument 224 relative to instrument holder 200 can be zeroed. For example, a user of system 100 can press a button or activate a switch on control device 222 or human interface devices 145. Thus, the position of instrument 224 and tip 232 can be recorded in surgical system 100 for referencing in the coordinate system of robotic arm 120. Calibration module 216 can be removed from instrument holder 200 at step 516.

Thus, steps 512-516 can describe a method of calibrating measuring device 204.

At step 518, robotic arm 120 can be positioned relative to patient 312 to position instrument holder 200 at a desired trajectory toward patient 312. In additional examples, robotic arm 120 can be positioned before other steps of the method, such as before steps 506 and 508 where calibration module 216 and instrument adapter 214 are coupled to instrument holder 200.

At step 520, instrument 224 can be translated within passage 226 along axis 208 toward patient 312. Translation of instrument 224 can cause movement of tip 232 beyond the position of engagement with plate 262 when plate 262 was attached. Wheel 282 can rotate an amount corresponding to the movement of instrument 224. For example, the linear translation of instrument 224 can correspond to an arc length about the circumference of wheel 282.

At step 522, a measurement of wheel 282 can be obtained using sensor 296. Sensor 296 can correlate the circumferential rotation of wheel 282 to the linear distance that instrument 224 has traversed to determine a position of tip 232 relative to the zeroed position. Such position can be correlated back to the coordinate system of surgical system 100 via the known position of robotic arm 120 in the coordinate system. The mechanical measurement can alternatively, or additionally be taken, using an encoder, such as encoder 322, to directly electro-mechanically measure the position of instrument 224.

At step 524, a medical procedure or a step of a medical procedure can be performed with instrument 2224 held in a desired orientation, such as an orientation according to a medical plan.

At step 526, instrument 224 and instrument adapter 214 can be removed from instrument holder 200. Subsequently, other surgical tasks can be performed by attaching a different instrument adapter to instrument holder 200, calibrating the different instrument with measuring device 204 and calibration module 216, and moving robotic arm 120 to a new position, such as by returning to step 506 or another step of method 500.

Steps 518-526 can describe a method of performing a medical procedure using instrument holder 200 and measuring device 204 to hold and track the position of instrument 224.

Figure 14:
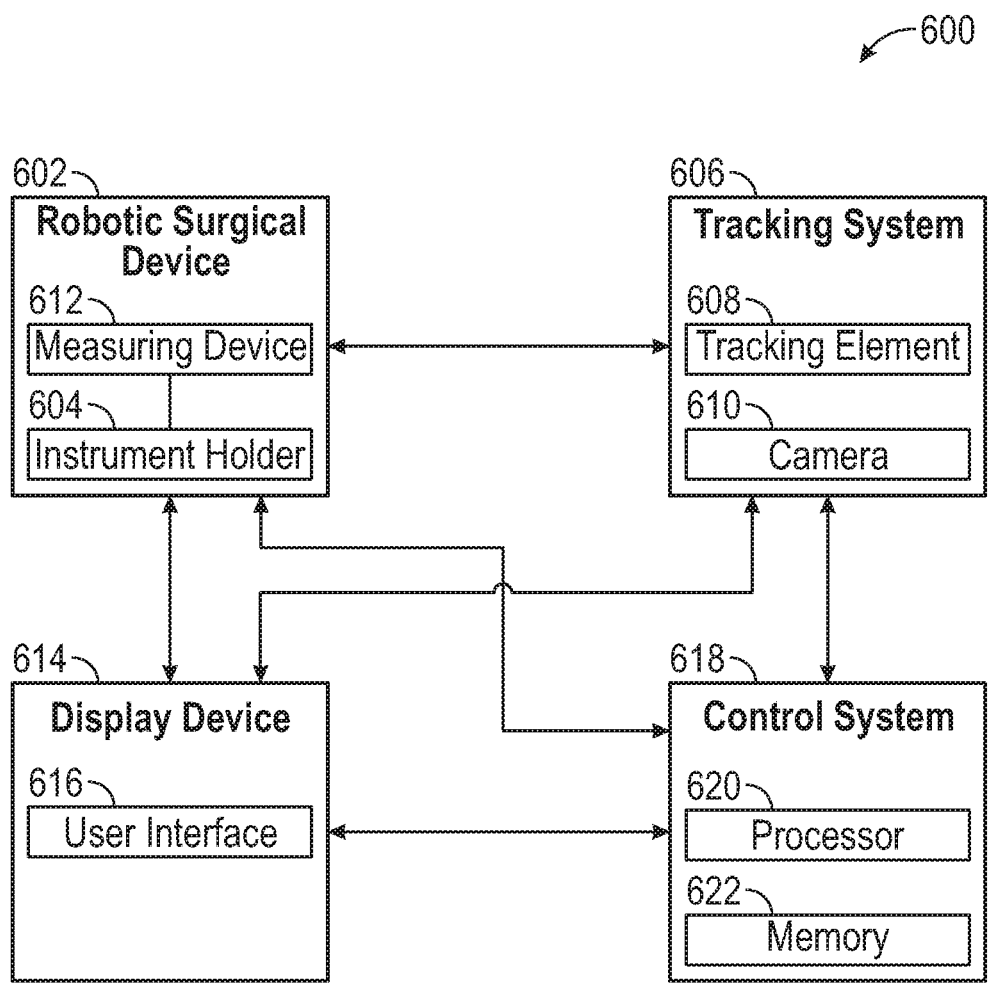
FIG. 14 is a schematic illustration of a robotic surgical system incorporating an instrument holder having a depth control device of the present application interacting with a tracking system.

FIG. 14 illustrates system 600 for performing techniques described herein, in accordance with some embodiments. System 600 is an example of a system that can incorporate surgical system 100 of FIG. 1. System 600 can include robotic surgical device 602 (e.g., robotic surgical device 115) coupled to instrument holder 604 (e.g., instrument holder 200), which may interact with tracking system 606. In other examples, the instrument holders described herein can be used without tracking system 606. Tracking system 606 can include tracking element 608 and camera 610. Instrument holder 604 can include measuring device 612 (e.g., measuring device 204). System 600 can include display device 614, which can be used to display user interface 616. System 600 can include control system 618 (e.g., a robotic controller or computing system 140 of FIG. 1), including processor 620 and memory 622. In an example, display device 614 can be coupled to one or more of robotic surgical device 602, tracking system 606, or control system 618. As such, data generated by measuring device 612 can be shared with control system 618, tracking system 606 and an operator of system 600 via display device 614. In examples, measuring device 612 can be operated without input from tracking system 608 such that robotic surgical device 602 can be positioned and tracked by 1) movement of robotic arm 120 within the native coordinate system of robotic arm 120 and 2) movement of surgical device 602 relative to instrument holder 604 using measuring device 612.

Figure 15:
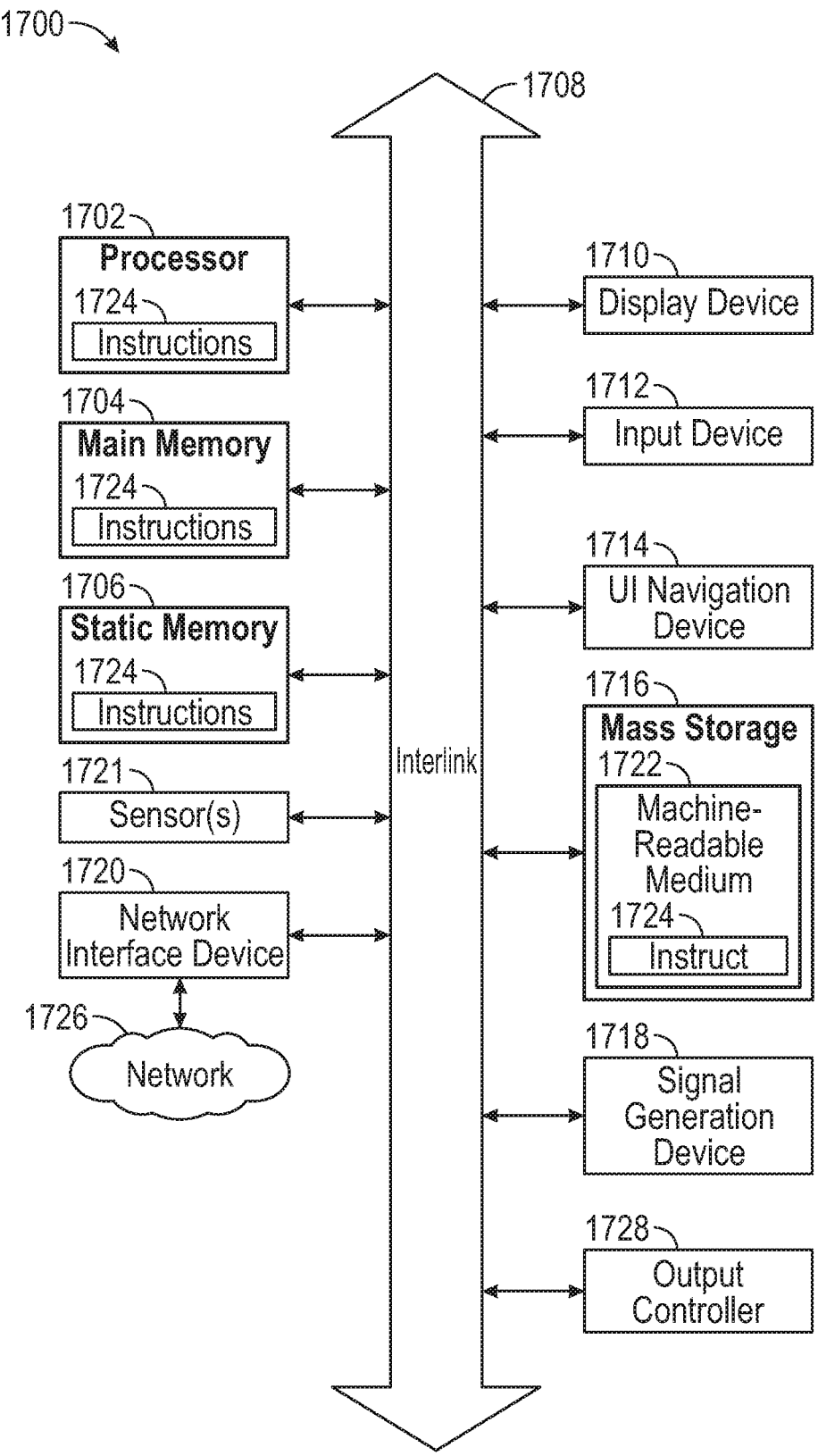
FIG. 15 is a schematic illustration of a block diagram of an example machine upon which any one or more of the techniques discussed herein may perform and with which any of the devices discussed herein may be used in accordance with some embodiments.

FIG. 15 illustrates a block diagram of an example machine 1700 upon which any one or more of the techniques discussed herein may perform in accordance with some embodiments. For example, machine 1700 can comprise computing system 140 of FIG. 1. Machine 1700 can comprise an example of a controller for robotic system 115 and sensors 1721 can include the measuring devices described herein, such as measuring device 204, and tracking elements 170 and 608. As such instructions 1724 can be executed by processor 1702 to generate and correlate position information to determine the position of a surgical instrument relative to robotic arm 120. For example, position information of measuring device 204 (e.g., sensor 1721) relating to the location of tip 232 relative to guide body 202 can be stored in main memory 1704 and accessed by processor 1702. Processor 1702 can also receive input (such as at input device 1712) relating to the position of instrument holder 200 relative to robotic arm 120 and store such information in main memory 1704. Processor 1702 can further relate position information of tip 232 to the position information of arm 120 to correlate the position of tip 232 to robotic arm 120, not just instrument holder 200. As such, as tip 232 moves machine 1700 can continuously track and update the location of tip 232 relative to robotic arm 120 via measuring device 204 and, for example, display said position on display device 1710 (e.g., user interface devices 145).

In alternative embodiments, machine 1700 may operate as a standalone device or may be connected (e.g., networked) to other machines. In a networked deployment, machine 1700 may operate in the capacity of a server machine, a client machine, or both in server-client network environments. In an example, machine 1700 may act as a peer machine in peer-to-peer (P2P) (or other distributed) network environment. Machine 1700 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Machine (e.g., computer system) 1700 may include hardware processor 1702 (e.g., a central processing unit (CPU), a graphics processing unit (GPU), a hardware processor core, or any combination thereof), main memory 1704 and static memory 1706, some or all of which may communicate with each other via interlink (e.g., bus) 1708. Machine 1700 may further include display unit 1710, alphanumeric input device 1712 (e.g., a keyboard), and user interface (UI) navigation device 1714 (e.g., a mouse). In an example, display unit 1710, input device 1712 and UI navigation device 1714 may be a touch screen display. Machine 1700 may additionally include storage device (e.g., drive unit) 1716, signal generation device 1718 (e.g., a speaker), network interface device 1720, and one or more sensors 1721, such as a global positioning system (GPS) sensor, compass, accelerometer, or other sensor. Machine 1700 may include output controller 1728, such as a serial (e.g., Universal Serial Bus (USB), parallel, or other wired or wireless (e.g., infrared (IR), near field communication (NEC), etc.) connection to communicate or control one or more peripheral devices (e.g., a printer, card reader, etc.).

Storage device 1716 may include machine readable medium 1722 on which is stored one or more sets of data structures or instructions 1724 (e.g., software) embodying or utilized by any one or more of the techniques or functions described herein. Instructions 1724 may also reside, completely or at least partially, within main memory 1704, within static memory 1706, or within hardware processor 1702 during execution thereof by machine 1700. In an example, one or any combination of hardware processor 1702, main memory 1704, static memory 1706, or storage device 1716 may constitute machine readable media.

While machine readable medium 1722 is illustrated as a single medium, the term "machine readable medium" may include a single medium or multiple media (e.g., a centralized or distributed database, and/or associated caches and servers) configured to store the one or more instructions 1724. The term "machine readable medium" may include any medium that is capable of storing, encoding, or carrying instructions for execution by machine 1700 and that cause machine 1700 to perform any one or more of the techniques of the present disclosure, or that is capable of storing, encoding or carrying data structures used by or associated with such instructions. Non-limiting machine readable medium examples may include solid-state memories, and optical and magnetic media.

Instructions 1724 may further be transmitted or received over communications network 1726 using a transmission medium via network interface device 1720 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, network interface device 1720 may include one or more physical jacks (e.g., Ethernet, coaxial, or phone jacks) or one or more antennas to connect to communications network 1726. In an example, network interface device 1720 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by machine 1700, and includes digital or analog communications signals or other intangible medium to facilitate communication of such software.

The systems, devices and methods discussed in the present application can be useful in performing robotic-assisted surgical procedures that utilize robotic surgical arms that can be coupled to instrument holders used to precisely align trajectories of instruments relative to anatomy of a patient registered to the space of an operating room. The present disclosure describes adjustable instrument holders that can remain mounted to a robotic surgical arm throughout a surgical procedure. The adjustable instrument holders can be adjusted to hold instruments of different sizes, e.g., different diameters, without removing the instrument holder form the robotic arm. The adjustable instrument holders can be easily and quickly manipulated to remove a first instrument of a first size and insert a second instrument of a second size, thereby decreasing time for performing a surgical procedure. The adjustable instrument holders can include passages that have variable orifice sizes, e.g., variable diameters, formed by adjustable members, such as jaws or blades, that form adjustable jaws, chucks or diaphragms to align an instrument and hold an instrument along a trajectory. The adjustable instrument holders can include adjustment members that provide axial length along an axis of the trajectory to provide stability to the instrument. The adjustable instrument holders can additionally be easily and quickly assembled and disassembled for cleaning, sanitizing and sterilizing procedures.

VARIOUS NOTES & EXAMPLES

Example 1 can include or use subject matter such as an instrument holder system that can comprise a guide body comprising a first end, a second end, and a passage extending between the first and second ends along an axis to receive an instrument; and a mechanical or electro-mechanical measuring device comprising an attachment body for coupling to the guide body, and a probe configured to extend into a trajectory of the passage to contact the instrument and generate positional data.

Example 2 can include, or can optionally be combined with the subject matter of Example 1, to optionally include a probe comprising a wheel configured to rotate about an axle. Example 3 can include, or can optionally be combined with the subject matter of one or any combination of Examples 1 or 2 to optionally include a probe further comprising a reader device configured to determine a rotational position of the wheel about the axle.

Example 4 can include, or can optionally be combined with the subject matter of one or any combination of Examples 1 through 3 to optionally include a reader device comprising a laser, and a wheel comprising marks configured to be read by the laser.

Example 5 can include, or can optionally be combined with the subject matter of one or any combination of Examples 1 through 4 to optionally include a reader device comprising an encoder embedded into the wheel or axle.

Example 6 can include, or can optionally be combined with the subject matter of one or any combination of Examples 1 through 5 to optionally include a sliding bracket coupled to the wheel, the sliding bracket being adjustable relative to the axis, and a biasing member configured to push the sliding bracket toward the axis.

Example 7 can include, or can optionally be combined with the subject matter of one or any combination of Examples 1 through 6 to optionally include a probe that further comprises a plurality of wheels each having an instrument contact surface, the instrument contact surfaces configured to surround the axis.

Example 8 can include, or can optionally be combined with the subject matter of one or any combination of Examples 1 through 7 to optionally include a wheel having teeth.

Example 9 can include, or can optionally be combined with the subject matter of one or any combination of Examples 1 through 8 to optionally include a motor configured to rotate the wheel.

Example 10 can include, or can optionally be combined with the subject matter of one or any combination of Examples 1 through 9 to optionally include a control device coupled to the probe and configured to receive the positional data.

Example 11 can include, or can optionally be combined with the subject matter of one or any combination of Examples 1 through 10 to optionally include a control device that comprises a transmitter configured to transmit the positional data via a signal to a surgical system. Example 12 can include, or can optionally be combined with the subject matter of one or any combination of Examples 1 through 11 to optionally include a transmitter that comprises a wireless signal transmitter.

Example 13 can include, or can optionally be combined with the subject matter of Example 12, to optionally include a guide body further comprising an instrument adapter configured to adjust a size of the passage.

Example 14 can include, or can optionally be combined with the subject matter of Example 13, to optionally include a calibration module comprising a first portion configured to couple to the second end of the guide body, and a plate extending from the first portion to oppose the second end of the guide body, wherein the plate is located a fixed distance from the second end of the guide body, a magnitude of the fixed distance being electronically stored in the control device.

Example 15 can include or use subject matter such as a method of determining a position of a surgical instrument relative to an instrument holder for a robotic arm comprising inserting an instrument into a passage of the instrument holder, moving the instrument into contact with a sensing element mounted to the instrument holder, moving a tip of the instrument out of the instrument holder to cause movement of the sensing element, and correlating movements of the sensing element to distances the tip extends out of the instrument holder.

Example 16 can include, or can optionally be combined with the subject matter of Example 15 to optionally include moving a tip of the instrument out of the instrument holder to cause movement of the sensing element by causing rotation of the sensing element.

Example 17 can include, or can optionally be combined with the subject matter of one or any Examples 15 and 16 to optionally include biasing the sensing element toward an axial center of the passage.

Example 18 can include, or can optionally be combined with the subject matter of one or any combination of Examples 15 through 17 to optionally include moving the instrument into contact with the sensing element by moving the instrument into frictional engagement with the sensing element or moving the instrument into meshed engagement with the sensing element.

Example 19 can include, or can optionally be combined with the subject matter of one or any combination of Examples 15 through 18 to optionally include calibrating a zero position for the tip of the instrument relative to the instrument holder.

Example 20 can include, or can optionally be combined with the subject matter of one or any combination of Examples 15 through 19 to optionally include calibrating the zero position for the tip by engaging the tip with a plate of a calibration module disposed opposite an outlet of the instrument holder.

Example 21 can include, or can optionally be combined with the subject matter of one or any combination of Examples 15 through 20 to optionally include correlating movements of the sensing element to distances the tip extends out of the instrument holder by reading rotation of the sensing element with a reader configured to identify hash marks on the sensing element.

Example 22 can include, or can optionally be combined with the subject matter of one or any combination of Examples 15 through 21 to optionally include correlating movements of the sensing element to distances the tip extends out of the instrument holder comprises reading rotation of a shaft of the sensing element with an encoder.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." in this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein," Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMS), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An instrument holder system comprising:
   a robotic arm configured to move an end effector to predetermined locations within a three-dimensional coordinate system;
   a coupler for attaching the end effector the robotic arm; and
   an instrument holder comprising the end effector, the instrument holder comprising:
      a guide body attached to the coupler, the guide body comprising:
         a first end;
         a second end; and
         a first passage extending between the first and second ends along an axis to receive an instrument; and
      a mechanical or electro-mechanical measuring device comprising:
         an attachment body for releasably coupling to an exterior of the guide body; and
         a probe configured to extend into a trajectory of the first passage to contact the instrument and generate positional data.

2. The instrument holder system of claim 1, wherein the guide body further comprises an instrument adapter configured to adjust a size of the first passage, wherein the instrument adapter comprises:
   an adapter tube configured to be inserted into the first passage of the guide body;
   a second passage extending through the adapter tube to receive the instrument; and
   a stop flange to prevent the adapter tube from passing through the first passage of the guide body via engagement with the first end;
   wherein the first passage of the guide body and the second passage of the adapter tube are concentrically aligned; and
   wherein the attachment body is attached to the second end at a bottom of the guide body.

3. The instrument holder system of claim 1, wherein the probe comprises a wheel configured to rotate about an axle.

4. The instrument holder system of claim 3, further comprising:
a sliding bracket coupled to the wheel, the sliding bracket being adjustable relative to the axis; and
a biasing member configured to push the sliding bracket toward the axis.

5. The instrument holder system of claim 3, wherein the probe further comprises a plurality of wheels each having an instrument contact surface, the instrument contact surfaces configured to surround the axis.

6. The instrument holder system of claim 3, wherein the wheel includes teeth.

7. The instrument holder system of claim 3, further comprising a motor configured to rotate the wheel.

8. The instrument holder system of claim 3, wherein the probe further comprises a reader device configured to determine a rotational position of the wheel about the axle.

9. The instrument holder system of claim 8, wherein:
the reader device comprises a laser, and
the wheel comprises marks configured to be read by the laser.

10. The instrument holder system of claim 8, wherein the reader device comprises an encoder embedded into the wheel or axle.

11. The instrument holder system of claim 1, further comprising:
a control device coupled to the probe and configured to receive the positional data; and
a robotic arm controller configured to communicate with the control device.

12. The instrument holder system of claim 11, further comprising a calibration module comprising:
a first portion configured to couple to the second end of the guide body; and
a plate extending from the first portion to oppose the second end of the guide body, wherein the first portion positions the plate in a path of the first passage to prevent instruments from passing through the guide body beyond the plate;
wherein the plate is located a fixed distance from the second end of the guide body so the probe can engage an instrument when extending beyond the guide body at the fixed distance, a magnitude of the fixed distance being electronically stored in the control device.

13. The instrument holder system of claim 11, wherein the control device comprises a transmitter configured to transmit the positional data via a signal to a surgical system and the robotic arm controller is configured to convert the positional data from the control device to coordinates for the three-dimensional coordinate system of the robotic arm.

14. The instrument holder system of claim 13, wherein the transmitter comprises a wireless signal transmitter.

15. The instrument holder system of claim 1, wherein the attachment body attaches to the second end of the guide body to position the probe away from an exit of the first passage in the guide body.

16. The instrument holder system of claim 15, wherein the guide body further comprises a flange extending from the second end and the attachment body is configured to attach to the flange.

17. The instrument holder system of claim 16, further comprising an instrument adapter insertable into the first end of the first passage so as to not interfere with the probe.

18. The instrument holder system of claim 17, further comprising a calibration module attachable to the flange.

19. A method of determining a position of a surgical instrument relative to an instrument holder for a robotic arm, the method comprising:
attaching the instrument holder to a robotic arm using a coupler, the robotic arm movable to predetermined locations within a three-dimensional coordinate system;
inserting an instrument into a passage of the instrument holder, the instrument holder comprising:
a guide body attached to the coupler, the guide body comprising:
a first end;
a second end; and
a first passage extending between the first and second ends along an axis to receive an instrument; and
a mechanical or electro-mechanical measuring device comprising:
an attachment body for releasably coupling to an exterior of the guide body; and
a probe configured to extend into a trajectory of the first passage to contact the instrument and generate positional data;
moving the instrument into contact with the probe;
moving a tip of the instrument out of the instrument holder to cause movement of the probe; and
correlating movements of the probe to distances the tip extends out of the instrument holder.

20. The method of claim 19, further comprising biasing the probe toward an axial center of the first passage.

21. The method of claim 19, further comprising calibrating a zero position for the tip of the instrument relative to the instrument holder, wherein calibrating the zero position for the tip comprises engaging the tip with a plate of a calibration module disposed opposite an outlet of the instrument holder.

22. The method of claim 19, wherein correlating movements of the probe to distances the tip extends out of the instrument holder comprises reading rotation of a shaft of the probe with an encoder or reading rotation of the probe with a reader configured to identify hash marks on the probe.

23. An instrument holder system comprising:
a guide body comprising:
a first end;
a second end; and
a first passage extending between the first and second ends along an axis to receive an instrument;
a mechanical or electro-mechanical measuring device comprising:
an attachment body for coupling to the guide body; and
a probe positioned proximate the second end of the guide body and configured to extend into a trajectory of the first passage to contact the instrument and generate positional data; and
an instrument adapter configured to adjust a size of the first passage, wherein the instrument adapter comprises:
an adapter tube configured to be inserted into the first passage of the guide body;
a second passage extending through the adapter tube to receive the instrument wherein the second passage of the instrument adapter has a smaller cross-sectional area than the first passage of the guide body; and
a stop flange to prevent the adapter tube from passing through the first passage of the guide body;
wherein the stop flange is configured to engage the first end of the guide body to position the adapter tube within the first passage spaced from the second end so as to not interfere with the probe; wherein the first passage of the guide body and the second passage of the adapter tube are concentrically aligned.

24. The instrument holder system of claim 23, further comprising a plurality of instrument adapters each having a different sized second passage.

\* \* \* \* \*